United States Patent
Lai et al.

(10) Patent No.: US 10,526,398 B2
(45) Date of Patent: Jan. 7, 2020

(54) ANTI-DENGUE VIRUS ANTIBODIES AND APPLICATIONS THEREOF

(71) Applicant: National Defense Medical Center, Taipei (TW)

(72) Inventors: Szu-Chia Lai, New Taipei (TW); Yu-Yine Huang, New Taipei (TW); Chang-Chi Lin, New Taipei (TW); Jiunn-Jye Wey, New Taipei (TW); Meng-Hung Tsai, Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 0 days.

(21) Appl. No.: 16/006,000

(22) Filed: Jun. 12, 2018

(65) Prior Publication Data

US 2019/0375826 A1    Dec. 12, 2019

(51) Int. Cl.
*C07K 16/10* (2006.01)
*G01N 33/569* (2006.01)

(52) U.S. Cl.
CPC ... *C07K 16/1081* (2013.01); *G01N 33/56983* (2013.01); *C07K 2317/31* (2013.01); *C07K 2317/565* (2013.01); *G01N 2333/185* (2013.01)

(58) Field of Classification Search
CPC .......... C07K 16/1081; C07K 2317/565; C07K 2317/31; G01N 33/56983; G01N 2333/185; G01N 2333/18; G01N 2469/20; G01N 2469/10; G01N 2500/02; G01N 2333/08; Y02A 50/386; Y02A 50/53; Y02A 50/394; Y02A 50/385; A61K 39/12; A61K 2039/505; A61K 39/42; A61K 38/00; A61K 2039/6075; A61K 38/162; A61K 35/76; A61K 47/6841; C12N 2770/24134; C12N 7/00; C12N 2770/24111; C12N 2770/24011

See application file for complete search history.

*Primary Examiner* — Rachel B Gill

(74) *Attorney, Agent, or Firm* — Birch, Stewart, Kolasch & Birch, LLP

(57) ABSTRACT

The present invention relates to anti-virus dengue virus antibodies and applications thereof. Specifically, the anti-virus dengue virus antibodies of the present invention are serotype specific and useful for specific detection and differentiation of various dengue virus serotypes in a biological sample. The present invention also provide methods and kits for detecting dengue virus and methods and compositions for use in diagnosis and treatment of dengue virus disease using the anti-virus dengue virus antibodies as described herein.

21 Claims, 9 Drawing Sheets

Specification includes a Sequence Listing.

| | Heavy chain | | |
|---|---|---|---|
| mAb | CDR1 | CDR2 | CDR3 |
| 1st Ab (12-4.1) | GYTFTSYWIH (SEQ ID NO: 2) | YITPNTGYNENSQKFRG (SEQ ID NO: 4) | RTYEGYLDV (SEQ ID NO: 6) |
| 2nd Ab (33-7.1) | GYTFTSYWMH (SEQ ID NO: 16) | YINPNTGFTEYSQKFKD (SEQ ID NO: 18) | ENYRYDGAMDY (SEQ ID NO: 20) |
| 3nd Ab (43-1.3) | GYSFSNYWMH (SEQ ID NO: 30) | VIDPSDSETRLNQKFKD (SEQ ID NO: 32) | SQFGLRFAY (SEQ ID NO: 34) |
| 4th Ab (22-1.5) | GYTFTDYNIH (SEQ ID NO: 44) | YIYPDNGDTGYNQIFKN (SEQ ID NO: 46) | RVLLDS (SEQ ID NO: 48) |
| 5th Ab (82-1.1) | GFTFSNYDMS (SEQ ID NO: 58) | AINSNGGSTYYPDSVKG (SEQ ID NO: 60) | PNGYGAMDY (SEQ ID NO: 62) |
| | Light chain | | |
| mAb | CDR1 | CDR2 | CDR3 |
| 1st Ab (12-4.1) | RSSQNLVHNNGNTYLE (SEQ ID NO: 9) | KVSNRLS (SEQ ID NO: 11) | FQASHVPRT (SEQ ID NO: 13) |
| 2nd Ab (33-7.1) | SVSSSVSSSNLH (SEQ ID NO: 23) | GTSTLAS (SEQ ID NO: 25) | QQWSSYPLT (SEQ ID NO: 27) |
| 3nd Ab (43-1.3) | QSSQSLFNSGTQKNYLT (SEQ ID NO: 37) | WASTRDS (SEQ ID NO: 39) | QNDYDSPYT (SEQ ID NO: 41) |
| 4th Ab (22-1.5) | SASQDINNFLN (SEQ ID NO: 51) | YTSSLQS (SEQ ID NO: 53) | QQYSKLPRT (SEQ ID NO: 55) |
| 5th Ab (82-1.1) | KSRQSLLDSDGKTYLN (SEQ ID NO: 65) | LVSKLDS (SEQ ID NO: 67) | LQATHFPWT (SEQ ID NO: 69) |

Fig. 7 mAb12-4.1 heavy chain amino acid sequence (SEQ ID NO: 71):
EVKLQESGAELAKPGASVKMSCRASGYTFTSYWIHWVKERPGQGLEWIG
YITPNTGYNENSQKFRGKATLTADKSSNTAYMQLSSLTSEDSAVYFCVR
RTYEGYLDVWGAGTTVTVSS mAb12-4.1 light chain amino acid sequence (SEQ ID NO: 72):
DIVMTQTPLSLPVSLGDQASISCRSSQNLVHNNGNTYLEWYLQKPGQSP
KLLIYKVSNRLSGVPDRFSGSGSGTDFTLNISRVEAEDLGIYYCFQASH
VPRTFGGGTKLEIKR mAb33-7.1 heavy chain amino acid sequence (SEQ ID NO: 73):
EVQLQESGAELAKPGASVKMSCKASGYTFTSYWMHWVKQRPGQVLEWIG
YINPNTGFTEYSQKFKDKATLTAVKSSSTAYIQLTSLTSDDSAVYYCAR
ENYRYDGAMDYWGQGTSVTVSS mAb33-7.1 light chain amino acid sequence (SEQ ID NO: 74):
DIVLTQSPALMAAFPGDRVTITCSVSSSVSSSNLHWYQQKSETSPKPWI
YGTSTLASGVPVRFSGSGSGTSYSLTISSMEAEDAATYYCQQWSSYPLT
FGAGTKLELKR mAb43-1.3 heavy chain amino acid sequence (SEQ ID NO: 75):
GELQESGPQVVRPGTSVKISCKASGYSFSNYWMHWVKQRPGQGLEWIGV
IDPSDSETRLNQKFKDKATLTVDKSSSTAYMQLSSPTSEDSAIYYCARS
QFGLRFAYWGQGTLVTVSA mAb43-1.3 light chain amino acid sequence (SEQ ID NO: 76):
DIVMTQSPSSMTVTAGEKVTMSCQSSQSLFNSGTQKNYLTWYQQKPGQP
PKLLISWASTRDSGVPDRFTGSGSGTDFTLTINGVQAEDLAVYFCQNDY
DSPYTFGGGTKLEIKR mAb22-1.5 heavy chain amino acid sequence (SEQ ID NO: 77):
EVQLQQSGPELVKPGASVKISCKASGYTFTDYNIHWVKQSPGKSLEWIG
YIYPDNGDTGYNQIFKNKATLTVDTSSSAAYMELRSLTSEDSAVYYCVR
RVLLDSWGQGTSVTVSS mAb22-1.5 light chain amino acid sequence (SEQ ID NO: 78):
DIQMTQTTSSLSASLGDRVTISCSASQDINNFLNWYQQKPDGTIKLLIY
YTSSLQSGVPSRFSGSGSGTDYSLTISNLEPEDIATYYCQQYSKLPRTF
GGGTKLEIKR mAb82-1.2 heavy chain amino acid sequence (SEQ ID NO: 79):
EVQLQQSGGGLVQPGGSLKLSCAASGFTFSNYDMSWIRQTPDKRLEMVA
AINSNGGSTYYPDSVKGRFTISRDKAKNTLYLQMSSLKSEDTAMYYCAS
PNGYGAMDYWGQGTSVTVSS mAb82-1.2 light chain amino acid sequence (SEQ ID NO: 80):
DIVITQTPLTLSVTIGQPASISCKSRQSLLDSDGKTYLNWLLQRPGESP
KLLIYLVSKLDSGVPDRFTGSGSGTDFTLKISRVEAEDLGVYYCLQATH
FPWTFGGGTKLEIKRA

Fig. 8

ANTI-DENGUE VIRUS ANTIBODIES AND APPLICATIONS THEREOF

TECHNOLOGY FIELD

The present invention relates to anti-virus dengue virus antibodies and applications thereof. Specifically, the anti-virus dengue virus antibodies of the present invention are serotype specific and useful for specific detection and differentiation of various dengue virus serotypes in a biological sample. The present invention also provide methods and kits for detecting dengue virus and methods and compositions for use in diagnosis and treatment of dengue virus disease using the anti-virus dengue virus antibodies as described herein.

BACKGROUND OF THE INVENTION

Today about 3.9 billion of the world's population live in areas where there is a risk of dengue transmission. An estimated 100 million dengue infection occur yearly, including 250,000-500,000 severe illness cases and around 25,000 deaths. Dengue is a mosquito-borne viral disease that is caused by transmission of any one of the four dengue virus serotypes (DENV1, DENV2, DENV3, and DENV4). Globally, dengue fever is predominantly spread by two major mosquito vectors: *Aedes aegypti* (urban-adapted) and *Aedes albopictus*. The rapid spread of dengue is attributed to urbanization in tropical and subtropical countries, increasing travel within and between endemic countries, and ineffective vector control strategies. Indeed, the disease and economic burden of dengue fever have become a global public health problem.

As so far, no effective antiviral agents are currently available to treat dengue infection and vaccine still in the phase of evaluation. Furthermore, infection with one serotype of dengue virus confers lifelong immunity to the same serotype but increases the risk of developing severe dengue when infected with another serotype. Therefore, the diagnosis of DENY in early stage is very important for disease management. The early diagnosis of dengue virus infection would provide intervention to treat patients and control the epidemics. People infected with the dengue virus exhibit a wide range of clinical presentations, ranging from asymptomatic infections to severe dengue fever, making accurate diagnoses difficult. Current laboratory diagnostic tests for dengue include isolating the virus, viral RNA detection, antigen detection, and serological methods. Virus isolation and viral RNA detection are effective during first five (5) days of illness; both methods can identify the serotype of dengue virus. However, virus isolation is time consuming and viral RNA detection requires special equipment and training personnel. Anti-DENV IgM or IgG antibodies merely appear in blood until 5 days post illness onset and may cross react with other flaviviruses; therefore detection of anti-DENY IgM or IgG is not useful in confirming the presence of the virus during the first 5 days of symptoms and false-positive results could occur frequently.

During the acute phase of the disease (i.e. between days 1 and 7 that follow the onset of illness), dengue virus nonstructural protein 1 (NS1), a 50 kDa glycoprotein, is secreted and accumulate to high concentrations in the blood sera of patients. The presence of NS1 in human sera can be confirmed between 1 and 9 days after infection. In addition, NS1 can be detected when viral RNA is not detectable by RT-PCR and before IgM antibodies appear. NS1 proteins are good target to be an early diagnostic marker. The NS1 antigen detection assays could be performed with simple, low cost, handle large of samples and rapid methods in early diagnosis of DENY. However, although several commercial NS1 detection tests are available to diagnose dengue during the early stages of disease, none of them can differentiate among various dengue serotypes.

There remains a need to develop a diagnostic approach that can detect and differentiate among various dengue serotypes.

SUMMARY OF THE INVENTION

The present invention is based on the identification of a number of isolated antibodies, which unexpectedly exhibit superior specificity for respective dengue virus serotypes. Each of the serotype specific antibody of the present invention is capable of detecting one specific serotype of dengue virus without substantially cross reacting with other serotypes. The present invention provides such antibodies and antigen-binding fragment thereof and also compositions and kits comprising the same and methods using the same. The present invention is useful for specific detection of one or more serotypes of dengue virus in a sample, particularly a sample from a patient suspected to be infected by the virus. The present invention also provides a cross reactive antibody specific to dengue virus (all serotypes), which can be paired with any of the serotype specific antibody as described herein for use in an immunoassay for detecting dengue virus in a sample.

In one aspect, the present invention provides an isolated antibody or antigen-binding fragment thereof, wherein the isolated antibody is selected from the group consisting of:

(i) a first antibody specific for dengue virus serotype 1 (DENV1) comprising
  (a) a heavy chain variable region ($V_H$) which comprises a heavy chain complementary determining region (HC CDR1) of SEQ ID NO: 2, a heavy chain complementary determining region 2 (HC CDR2) of SEQ ID NO: 4, and a heavy chain complementary determining region 3 (HC CDR3) of SEQ ID NO: 6; and
  (b) a light chain variable region ($V_L$) which comprises a light chain complementary determining region 1 (LC CDR1) of SEQ ID NO: 9, a light chain complementary determining region (LC CDR2) of SEQ ID NO: 11, and a light chain complementary determining region 3 (LC CDR3) of SEQ ID NO: 13;

(ii) a second antibody specific for dengue virus serotype 2 (DENV2) comprising
  (a) a $V_H$ which comprises a HC CDR1 of SEQ ID NO: 16, a HC CDR2 of SEQ ID NO: 18, and a HC CDR3 of SEQ ID NO: 20; and
  (b) a $V_L$ which comprises a LC CDR1 of SEQ ID NO: 23, a LC CDR2 of SEQ ID NO: 25, and a LC CDR3 of SEQ ID NO: 27;

(iii) a third antibody specific for dengue virus serotype 3 (DENV3) comprising
  (a) a $V_H$ which comprises a HC CDR1 of SEQ ID NO: 30, a HC CDR2 of SEQ ID NO: 32, and a HC CDR3 of SEQ ID NO: 34; and
  (b) a $V_L$ which comprises a LC CDR1 of SEQ ID NO: 37, a LC CDR2 of SEQ ID NO: 39, and a LC CDR3 of SEQ ID NO: 41;

(iv) a fourth antibody specific for dengue virus serotype 4 (DENV4) comprising
  (a) a $V_H$ which comprises a HC CDR1 of SEQ ID NO: 44, a HC CDR2 of SEQ ID NO: 46, and a HC CDR3 of SEQ ID NO: 48; and (b) a $V_L$ which comprises a LC CDR1 of SEQ ID NO: 51, a LC CDR2 of SEQ ID NO: 53, and a LC CDR3 of SEQ ID NO: 55;

(v) a fifth antibody cross-reactive to DENV1, DENV2, DENV3 and DENV4 comprising (a) a $V_H$ which comprises a HC CDR1 of SEQ ID NO: 58, a HC CDR2 of SEQ ID NO: 60, and a HC CDR3 of SEQ ID NO: 62; and (b) a $V_L$ which comprises a LC CDR1 of SEQ ID NO: 65, a LC CDR2 of SEQ ID NO: 67, and a LC CDR3 of SEQ ID NO: 69; and (vi) any combination of (i) to (v).

In some embodiments, the first antibody comprises a $V_H$ comprising SEQ ID NO: 71 and a $V_L$ comprising SEQ ID NO: 72.

In some embodiments, the second antibody comprises a $V_H$ comprising SEQ ID NO: 73 and a $V_L$ comprising SEQ ID NO: 74.

In some embodiments, the third antibody comprises a $V_H$ comprising SEQ ID NO: 75 and a $V_L$ comprising SEQ ID NO: 76.

In some embodiments, the fourth antibody comprises a $V_H$ comprising SEQ ID NO: 77 and a $V_L$ comprising SEQ ID NO: 78.

In some embodiments, the fifth antibody comprises a $V_H$ comprising SEQ ID NO: 79 and a $V_L$ comprising SEQ ID NO: 80.

The dengue virus specific antibodies of the present invention can be a full-length antibody. The antigen-binding fragment of the antibodies of the present invention can be scFv, (scFv)2, Fab, Fab', F(ab')$^2$.

In another aspect, the present invention provides a nucleic acid comprising a nucleotide sequence encoding an antibody heavy chain variable region ($V_H$) or an antibody light chain variable region ($V_L$) or both, wherein the $V_H$ and $V_L$ are as described herein.

The present invention also provides a vector (e.g. an expression vector) comprising any of the nucleic acids described herein and a host cell comprising such a vector.

The present invention further provides a method for preparing an antibody specific for dengue virus, comprising (i) culturing the host cell as described herein under conditions allowing for expression of the antibody, and optionally (ii) harvesting the antibody from the cell culture.

In a further aspect, the present invention provides a composition comprising (a) any of the antibody specific for dengue virus as described herein, any of the nucleic acids as described herein, or any of the vectors as described herein; and (b) a carrier e.g. a pharmaceutically acceptable carrier.

In some embodiments, the composition of the present invention is a pharmaceutical composition for use in treatment of dengue virus disease.

In some embodiments, the composition of the present invention is a diagnostic composition for use in diagnosis of dengue virus disease.

In still another aspect, the present invention provides a method for detecting dengue virus in a sample suspected of containing said dengue virus, comprising contacting the sample with an isolated antibody or antigen-binding fragment thereof specific for dengue virus, as described herein, and assaying binding of the antibody with the sample. The binding results are to determine the presence of respective dengue virus serotypes in the sample. Specifically, (i) binding of the first antibody with the sample is an indicative of the presence of DENV1 in the sample; (ii) binding of the second antibody with the sample is an indicative of the presence of DENV2 in the sample; (iii) binding of the third antibody with the sample is an indicative of the presence of DENV3 in the sample; and/or (iv) binding of the fourth antibody with the sample is an indicative of the presence of ENV4 in the sample. In some embodiments, the respective serotype specific antibody of the present invention is paired with a partner antibody to perform a sandwich assay.

In further another aspect, the present invention provides a kit for detecting the presence of one or more serotypes of dengue virus in a sample, comprising one or more serotype-specific antibodies to dengue virus as described herein and an optional partner antibody. The partner antibody can be a serotype cross-reactive antibody to dengue virus, for example, the fifth antibody as described herein.

In some embodiments, at least one of the antibodies in the kit comprises a detectable label.

Examples of the detectable label include but are not limited to an enzymatic label, a fluorescent label, a metal label and a radio label.

In some embodiments, the kit is an immunoassay kit.

Examples of the immunoassay include but are not limited to ELISA (enzyme-linked immunosorbent assay), RIA (radioimmunoassay), FIA (fluorescence immunoassay), LIA (luminescence immunoassay), or ILMA immunoluminometric assay.

In certain embodiments, the immunoassay is in a lateral flow assay format.

In particular, the immunoassay is a sandwich assay.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 6A shows the results of the ELISA test for sera of 17 patients infected with DENV1. FIG. 6B shows the result of the ELISA test for sera of 19 patients infected with DENV2. FIG. 6C shows the results of the ELISA test for sera of 16 patients infected with DENV3. FIG. 6D shows the results of the ELISA test for sera of 9 patients infected with DENV4. FIG. 6E shows the results of the ELISA test for sera of 5 patients with infected with DENVs. FIG. 6F shows the results of the ELISA test for sera of 80 other febrile patients. T/N ratios were calculated by dividing the OD450 value of patient serum by the average OD450 value of all negative healthy normal sera samples (i.e., patient serum OD450/mean OD450 of negative healthy normal sera). Samples were considered to be positive if their OD450 value was at least double the mean values of the negative controls.

FIG. 7 shows the CDR sequences of heavy chain and light chain the antibodies of the present invention.

FIG. 8 shows the sequences of heavy chain and light chain of the antibodies of the present invention.

DETAILED DESCRIPTION OF THE INVENTION

Figure 1A:
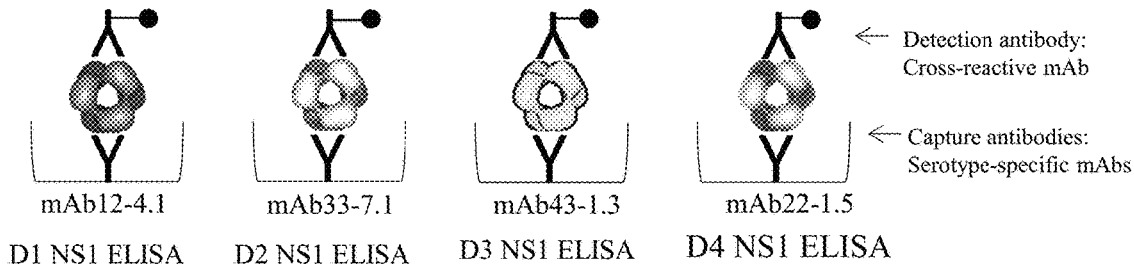
FIG. 1A shows the basic design of the sandwich (capture) ELISA using the serotype-specific mAbs of the present invention as capture antibodies, paired with a serotype cross-reactive antibody to dengue virus as detection antibodies.

The present invention relates to anti-virus dengue virus antibodies which are serotype specific. The present invention provides such antibodies and antigen-binding fragments thereof, which are useful for specific detection and differentiation of various dengue virus serotypes in a biological sample. The present invention further provides methods and vectors for preparing the antibodies or antigen-binding fragments thereof, and also kits and compositions comprising the same and methods using the same for detection of dengue virus and diagnosis and treatment of dengue virus disease. The present invention further provides a cross reactive antibody specific to dengue virus, which can be paired with any of the serotype specific antibody as described herein for use in an immunoassay for detecting dengue virus in a sample.

The following description is merely intended to illustrate various embodiments of the invention. As such, specific embodiments or modifications discussed herein are not to be construed as limitations to the scope of the invention. It will be apparent to one skilled in the art that various changes or equivalents may be made without departing from the scope of the invention.

I. Definitions

In order to provide a clear and ready understanding of the present invention, certain terms are first defined. Additional definitions are set forth throughout the detailed description. Unless defined otherwise, all technical and scientific terms used herein have the same meanings as is commonly understood by one of skill in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

The term "comprise" or "comprising" is generally used in the sense of include/including which means permitting the presence of one or more features, ingredients or components. The term "comprise" or "comprising" encompasses the term "consists" or "consisting of."

As used herein, the term "polypeptide" refers to a polymer composed of amino acid residues linked via peptide bonds. The term "protein" typically refers to relatively large polypeptides. The term "peptide" typically refers to relatively short polypeptides (e.g., containing up to 100, 90, 70, 50, 30, or 20 amino acid residues).

As used herein, the term "about" or "approximately" refers to a degree of acceptable deviation that will be understood by persons of ordinary skill in the art, which may vary to some extent depending on the context in which it is used. In general, "about" or "approximately" may mean a numeric value having a range of ±10% around the cited value.

As used herein, the term "substantially identical" refers to two sequences having 80% or more, preferably 85% or more, more preferably 90% or more, even more preferably 95% or more homology.

As used herein, the term "antibody" (interchangeably used in plural form) means an immunoglobulin molecule having the ability to specifically bind to a particular target antigen. As used herein, the term "antibody" includes not only intact (i.e. full-length) antibody molecules but also antigen-binding fragments thereof retaining antigen binding ability e.g. Fab, Fab', F(ab')2 and Fv. Such fragments are also well known in the art and are regularly employed both in vitro and in vivo. The term "antibody" also includes humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies.

An intact or complete antibody comprises two heavy chains and two light chains. Each heavy chain contains a variable region ($V_H$) and a first, second and third constant regions ($C_H1$, $C_H2$ and $C_H3$); and each light chain contains a variable region ($V_L$) and a constant region ($C_L$). The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light chains and those of heavy chains are responsible for antigen binding. The variables region in both chains generally contain three highly variable regions, called the complementarity determining regions (CDRs); namely, light (L) chain CDRs including LC CDR1, LC CDR2, and LC CDR3, and heavy (H) chain CDRs including HC CDR1, HC CDR2, HC CDR3). The three CDRs are franked by framework regions (FR1, FR2, FR3, and FR4), which are more highly conserved than the CDRs and form a scaffold to support the hypervariable regions. The constant regions of the heavy and light chains are not responsible for antigen binding, but involved in various effector functions. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively.

As used herein, the term "antigen-binding domain" or "antigen-binding fragment" refers to a portion or region of an intact antibody molecule that is responsible for antigen binding. An antigen-binding fragment is capable of binding to the same antigen to which the parent antibody binds. Examples of antigen-binding fragments include, but are not limited to: (i) a Fab fragment, which can be a monovalent fragment composed of a $V_H$-$C_H1$ chain and a $V_L$-$C_L$ chain; (ii) a F(ab')2 fragment which can be a bivalent fragment composed of two Fab fragments linked by a disulfide bridge at the hinge region; (iii) a Fv fragment, composed of the $V_H$ and $V_L$ domains of an antibody molecule associated together by noncovalent interaction; (iv) a single chain Fv (scFv), which can be a single polypeptide chain composed of a $V_H$ domain and a $V_L$ domain through a peptide linker; and (v) a (scFv)$_2$, which can comprise two $V_H$ domains linked by a peptide linker and two $V_L$ domains, which are associated with the two $V_H$ domains via disulfide bridges.

As used herein, the term "chimeric antibody" refers to an antibody containing polypeptides from different sources, e.g., different species. In some embodiments, in these chimeric antibodies, the variable region of both light and heavy chains may mimic the variable region of antibodies derived from one species of mammal (e.g., a non-human mammal such as mouse, rabbit and rat), while the constant portions may be homologous to the sequences in antibodies derived from another mammal such as a human.

As used herein, the term "humanized antibody" refers to an antibody comprising a framework region from a human antibody and one or more CDRs from a non-human (usually a mouse or rat) immunoglobulin.

As used herein, the term "human antibody" refers to an antibody in which essentially the entire sequences of the light chain and heavy chain sequences, including the complementary determining regions (CDRs), are from human genes. The human antibodies may include one or more amino acid residues not encoded by human germline immunoglobulin sequences e.g. by mutations in one or more of the CDRs, or in one or more of the FRs, so as to, for example, decrease possible immunogenicity, increase affinity, eliminate cysteines that might cause undesirable folding, etc.

As used herein, an "isolated" substance means that it has been altered by the hand of man from the natural state. In some embodiments, the polypeptide (e.g. antibody) or nucleic acids of the present invention can be said to be "isolated" or "purified" if they are substantially free of cellular material or chemical precursors or other chemicals/components that may be involved in the process of peptides/nucleic acids preparation. It is understood that the term "isolated" or "purified" does not necessarily reflect the extent to which the peptide has been "absolutely" isolated or purified e.g. by removing all other substances (e.g., impurities or cellular components). In some cases, for example, an isolated or purified polypeptide includes a preparation containing the polypeptide having less than 50%, 40%, 30%, 20% or 10% (by weight) of other proteins (e.g. cellular proteins), having less than 50%, 40%, 30%, 20% or 10% (by volume) of culture medium, or having less than 50%, 40%, 30%, 20% or 10% (by weight) of chemical precursors or other chemicals/components involved in synthesis procedures.

As used herein, the term "specific binds" or "specifically binding" refers to a non-random binding reaction between two molecules, such as the binding of the antibody to an epitope of its target antigen. An antibody that "specifically binds" to a target antigen or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen or an epitope than it does with other targets/epitopes. An antibody "specifically binds" to a target antigen if it binds with greater affinity, avidity, more readily, and/or with greater duration than it binds to other substances. In other words, it is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means specific/preferential binding. The affinity of the binding is defined in terms of a dissociation constant ($K_D$). Typically, specifically binding when used with respect to an antibody can refer to an antibody that specifically binds to (recognize) its target with an KD value less than about $10^{-7}$ M, such as about $10^{-8}$M or less, such as about $10^{-9}$ M or less, about $10^{-10}$ M or less, about $10^{-11}$ M or less, about $10^{-12}$ M or less, or even less, and binds to the specific target with an affinity corresponding to a $K_D$ that is at least ten-fold lower than its affinity for binding to a non-specific antigen (such as BSA or casein), such as at least 100 fold lower, for instance at least 1,000 fold lower, such as at least 10,000 fold lower.

As used herein, the term "cross-reactive" can refer to the ability of an antibody to react with similar antigenic sites on different proteins. For example, a cross-reactive antibody to dengue virus serotypes may mean that such antibody can cross react with (i.e. the antibody binding to) more than one serotype of dengue virus (e.g. all the four serotypes of dengue virus) or even other flavivirus e.g. Zika virus and/or Japanese encephalitis virus, instead of specifically react with only one certain serotype of dengue virus.

Dengue virus is a single-stranded RNA virus that is a member of the family Flaviviridae, genus Flavivirus. Dengue virus, as used herein, refers to any serotype of dengue virus, including dengue virus serotype 1 (DENV1), dengue virus serotype 2 (DENV2), dengue virus serotype 3 (DENV3) and dengue virus serotype 4 (DENV4). Those distinct dengue virus serotypes are genetically related but antigenically distinct. Immunity is serotype specific and there is no cross protection between the serotypes that infection with one serotype cannot protect human against the other serotypes. The serotypes can be determined by conventional methods known in the art such as RT-PCR using specific primer sets (TS1, TS2, TS3 or TS4, together with D1) to amplify serotype-specific fragments from the regions encoding the capsid and membrane proteins of dengue virus, as described in, for example, Konogoi et al. Virology Journal (2016) 13:182. Typical strains of each dengue virus serotype are available in this art, for example, DENV1 Hawaii, DENV2 16681, DENV3 H87, and DENV4 H241.

As used herein, the term "dengue virus disease" or "dengue" means a disease caused by dengue virus infection, typically transmitted by mosquitoes. People with dengue virus infection may experience no signs, or symptoms from mild to severe. When symptoms occur, they typically begin three to fourteen days after infection. Classic dengue fever (DF) frequently presents with fever, headache, severe muscle and joint pains, nausea and skin rash, while severe forms (DHF/DSS) are characterized by all the symptoms of DF, in combination with hemorrhagic manifestations (bleeding from gums or nose, in urine, stools, or under the skin), severe abdominal pain, persistent vomiting, fatigue, irritability or restlessness, which can be life-threatening without prompt treatment.

The terms "NS1," "NS1 polypeptide" and "NS1 protein" are used herein interchangeably. NS1 refers to a nonstructural glycoprotein encoded by dengue virus, which associates with the membrane on the cell surface and is eventually released into the circulation as early as 1 day post-onset of symptoms and detectable at least until about 9 days after infection. Therefore, NS1 makes it a good marker for diagnosis of dengue infection, especially in very early stage. The mature form of NS1 contains 352 amino acid residues, having a molecule weight of around 40 kDa or more depending on the glycosylation level. NS1 is serotype specific and the amino acid sequences of NS1 from different dengue virus serotypes are known and available in this art, for example, SEQ ID NO: 91 for NS1 from DENV1 (DENV1 NS1), SEQ ID NO: 92 for NS1 from DENV2 (DENV2 NS1), SEQ ID NO: 93 for NS1 from DENV3 (DENV3 NS1), and SEQ ID NO: 94 for NS1 from DENV4 (DENV1 NS1). NS1 can be prepared by a recombinant method as known in the art, or alternatively can be produced and harvested from the culture supernatant of dengue virus e.g. DENV1 Hawaii for producing DENV1 NS1, DENV2 16681 for producing DENV2 NS1, DENV3 H87 for producing DENV3 NS1, and DENV4 H241 for producing DENV4 NS1.

TABLE 1 shows exemplified amino acid sequence ofNS1 of DENV1, DENV2, DENV3 and DENV4.

| Dengue virus type 1 strain Hawaii | NS1 | DSGCVINWKG RLSAAIGKAW ENDMKFTVVV AKIIGADVQN GIFTTNIWLK WIESEKNETW MITPKIYGGP EGTTVVVDEH LRFKGEDGCW (SEQ ID NO: 91) | RELKCGSGIF EEGVCGIRSA GDVSGILTQG TTFIIDGPNT LRDSYTQVCD KLARASFIEV ISQHNYRPGY CGNRGPSLRT YGMEIRPVKD | VTNEVHTWTE TRLENIMWKQ RKMIGPQPME PECPDDQRAW PRLMSAAIKD KTCVWPKSHT STQTAGPWHL TTVTGKIIHE KEENLVKSLV | QYKFQADSPK ISNELNHILL HKYSWKSWGK NIWEVEDYGF SKAVHADMGY LWSNGVLESE GKLELDFDLC WCCRSCTLPP SA |
| Dengue virus type 2 strain 16681 | NS1 | DSGCVVSWKN KLASAIQKAH ENEVKLTIMT AKMLSTESHN GVFTTNIWLK WIESALNDTW MIIPKNLAGP DGTTVVVTED LRYRGEDGCW (SEQ ID NO: 92) | KELKCGSGIF EEGICGIRSV GDIKGIMQAG QTFLIDGPET LKEKQDVFCD KIEKASFIEV VSQHNYRPGY CGNRGPSLRT YGMEIRPLKE | ITDNVHTWTE TRLENLMWKQ KRSLRPQPTE AECPNTNRAW SKLMSAAIKD KNCHWPKSHT HTQITGPWHL TTASGKLITE KEENLVNSLV | QYKFQPESPS ITPELNHILS LKYSWKTWGK NSLEVEDYGF NRAVHADMGY LWSNGVLESE GKLEMDFDFC WCCRSCTLPP TA |
| Dengue virus type 3 strain H87 | NS1 | DMGCVINWKG RLATAIAGAW ENNIKLTVVV AKIVTAETQN GVFTTNIWLK WIESQKNGSW MIIPKSLAGP EGTTVVISEN LRYMGEDGCW (SEQ ID NO: 93) | KELKCGSGIF ENGVCGIRST GDITGVLEQG SSFIIDGPST LREVYTQLCD KLEKASLIEV ISQHNHRPGY CGTRGPSLRT YGMEIRPINE | VTNEVHTWTE TRMENLLWKQ KRTLTPQPME PECPSASRAW HRLMSAAVKD KTCTWPKSHT HTQTAGPWHL TTVSGKLIHE KEENMVKSLA | QYKFQADSPK IANELNYILW LKYSWKTWGK NVWEVEDYGF ERAVHADMGY LWSNGVLESD GKLELDFNYC WCCRSCTLPP SA |
| Daigue virus type 4 strain H241 | NS1 | DTGCAVSWSG RLASAILNAH EGGHDLTVVA AKIFTPEAKN GMFTTNIWMK WIESSKNQTW MLIPKAYAGP | KELKCGSGIF KDGVCGIRST GDVKGVLSKG STFLIDGPDT FREGSSEVCD QIEKASLIEV FSQHNYRQGY | VIDNVHTWTE TRLENIMWKQ KRALAPPVND SECPNERRAW HRLMSAAIKD KTCLWPKTHT ATQTVGPWHL | QYKFQPESPA ITNELNYVLW LKYSWKTWGK NFLEVEDYGF QKAVHADMGY LWSNGVLESQ GKLEIDFGEC |

TABLE 1-continued shows exemplified amino acid sequence of NS1 of DENV1, DENV2, DENV3 and DENV4.

PGTTVTIQED CDHRGPSLRT TTASGKLVTQ WCCRSCTMPP
LRFLGEDGCW YGMEIRPLSE KEENMVKSQV SA
(SEQ ID NO: 94)

The term "nucleic acid" or "polynucleotide" can refer to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide when the nucleotide sequence of the first polynucleotide is identical to the nucleotide sequence of the polynucleotide binding partner of the second polynucleotide. Thus, the polynucleotide whose sequence 5'-TATAG-3' is complementary to a polynucleotide whose sequence is 5'-CTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a given sequence of nucleotides (i.e., rRNA, tRNA and mRNA) or a given sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" encompasses all nucleotide sequences that are degenerate versions of each other and that encode the same amino acid sequence.

The term "recombinant nucleic acid" refers to a polynucleotide or nucleic acid having sequences that are not naturally joined together. A recombinant nucleic acid may be present in the form of a vector. "Vectors" may contain a given nucleotide sequence of interest and a regulatory sequence. Vectors may be used for expressing the given nucleotide sequence (expression vector) or maintaining the given nucleotide sequence for replicating it, manipulating it or transferring it between different locations (e.g., between different organisms). Vectors can be introduced into a suitable host cell for the above-described purposes. A "recombinant cell" refers to a host cell that has had introduced into it a recombinant nucleic acid. "A transformed cell" mean a cell into which has been introduced, by means of recombinant DNA techniques, a DNA molecule encoding a protein of interest.

Vectors may be of various types, including plasmids, cosmids, fosmids, episomes, artificial chromosomes, phages, viral vectors, etc. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprise, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, a secretion signal sequence (e.g., α-mating factor signal), a stop codon, and other control sequence (e.g., Shine-Dalgarno sequences and termination sequences). Preferably, vectors may further contain a marker sequence (e.g., an antibiotic resistant marker sequence) for the subsequent screening/selection procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes a tag for purpose of purification e.g. a His-tag.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom or conditions of the disorder, or a progression of the disorder, with the purpose to cure, heal, alleviate, relieve, alter, remedy, ameliorate, improve, or affect the disorder, the symptoms or conditions of the disorder, the disabilities induced by the disorder, or the progression of the disorder or the symptom or condition thereof.

The term "effective amount" used herein refers to the amount of an active ingredient to confer a desired biological effect in a treated subject or cell. The effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

II. Antibodies Specific to Dengue Virus

The present invention is based on the identification of a number of isolated antibodies with serotype specificity to dengue virus, including mAb12-4.1 (specific to DENV1), mAb33-7.1 (specific to DENV2), mAb43-1.3 (specific to DENV3), and mAb22-1.5 (specific to DENV4). These anti-dengue virus antibodies were found to be capable of recognizing one specific serotype of dengue virus without cross reacting with other serotypes. More specifically, these anti-dengue virus antibodies are specific for dengue virus NS1 protein of different serotypes; namely mAb12-4.1 is specific to the NS1 polypeptide originating from DENV1, mAb33-7.1 is specific to the NS1 polypeptide originating from DENV2, mAb43-1.3 is specific to the NS1 polypeptide originating from DENV3, and mAb22-1.5 is specific to the NS1 polypeptide originating from DENV4. These anti-dengue virus antibodies were found effective and workable in various forms of immunoassays to detect dengue virus in a sample with superior sensitivity and specificity. The present invention is also based on the identification of a cross reactive antibody specific to dengue virus, mAb 82-1.1, which is cross reactive to various serotypes of dengue virus, including DENV1, DENV2, DENV3, and DENV4, and can be paired with any of the serotype specific antibody as described herein for use in an immunoassay for detecting dengue virus in a sample.

Accordingly, described herein are serotype specific antibodies to dengue virus, including mAb12-4.1 (specific to DENV1), mAb33-7.1 (specific to DENV2), mAb43-1.3 (specific to DENV3) and mAb22-1.5 (specific to DENV4), and functional variants thereof. Also described herein is a cross reactive antibody specific to dengue virus, including mAb82-1.1 (cross reactive to DENV1, DENV2, DENV3, and DENV4), and functional variants thereof. The reactivity of these mAbs with DENV1-4 was determined using ELISA and Western blot. The characterizations of these mAbs are showed in Table 2. The amino acid sequences of the heavy chain variable region ($V_H$) and light chain variable region ($V_L$), and their complementary determining regions (CDR1, CDR2, CDR3), of each of mAb12-4.1, mAb33-7.1, mAb43-1.3, mAb22-1.5, and mAb 82-1.1, are as shown in Table 3 below.

A functional variant of mAb12-4.1 (specific to DENV1) (also referred to "a first antibody specific for DENV1" as described herein) can comprise (a) a heavy chain variable region ($V_H$) which comprises a heavy chain complementary determining region (HC CDR1) of SEQ ID NO: 2, a heavy chain complementary determining region 2 (HC CDR2) of SEQ ID NO: 4, and a heavy chain complementary determining region 3 (HC CDR3) of SEQ ID NO: 6; and (b) a light chain variable region ($V_L$) which comprises a light chain complementary determining region 1 (LC CDR1) of SEQ ID NO: 9, a light chain complementary determining region (LC CDR2) of SEQ ID NO: 11, and a light chain complementary determining region 3 (LC CDR3) of SEQ ID NO: 13, or an antigen-binding fragment thereof.

In some embodiments, the first antibody comprises a $V_H$ comprising SEQ ID NO: 71 or an amino acid sequence substantially identical thereto and a $V_L$ comprising SEQ ID NO: 72 or an amino acid sequence substantially identical thereto. Specifically, the first antibody includes a $V_H$ comprising an amino acid sequence has at least 80% (e.g. 82%, 84%, 85%, 86%, 88%, 90%, 92%, 94%, 95%, 96%, 98%, or 99%) identity to SEQ ID NO:71, and a $V_L$ comprising an amino acid sequence has at least 80% (e.g. 82%, 84%, 85%, 86%, 88%, 90%, 92%, 94%, 95%, 96%, 98%, or 99%) identity to SEQ ID NO:72. The first antibody also includes any recombinantly (engineered)-derived antibody encoded by the polynucleotide sequence encoding the relevant $V_H$ or $V_L$ amino acid sequences as described herein.

A functional variant of mAb33-7.1 (specific to DENV2) (also referred to "a second antibody specific for DENV2" as described herein) can comprise (a) a $V_H$ which comprises a HC CDR1 of SEQ ID NO: 16, a HC CDR2 of SEQ ID NO: 18, and a HC CDR3 of SEQ ID NO: 20; and (b) a VL which comprises a LC CDR1 of SEQ ID NO: 23, a LC CDR2 of SEQ ID NO: 25, and a LC CDR3 of SEQ ID NO: 27.

In some embodiments, the second antibody comprises a $V_H$ comprising SEQ ID NO: 73 or an amino acid sequence substantially identical thereto and a $V_L$ comprising SEQ ID NO: 74 or an amino acid sequence substantially identical thereto. Specifically, the second antibody includes a $V_H$ comprising an amino acid sequence has at least 80% (e.g. 82%, 84%, 85%, 86%, 88%, 90%, 92%, 94%, 95%, 96%, 98%, or 99%) identity to SEQ ID NO: 73, and a $V_L$ comprising an amino acid sequence has at least 80% (e.g. 82%, 84%, 85%, 86%, 88%, 90%, 92%, 94%, 95%, 96%, 98%, or 99%) identity to SEQ ID NO: 74. The second antibody also includes any recombinantly (engineered)-derived antibody encoded by the polynucleotide sequence encoding the relevant $V_H$ or $V_L$ amino acid sequences as described herein.

A functional variant of mAb43-1.3 (specific to DENV3) (also referred to "a third antibody specific for DENV3" as described herein) can comprise (a) a $V_H$ which comprises a HC CDR1 of SEQ ID NO: 30, a HC CDR2 of SEQ ID NO: 32, and a HC CDR3 of SEQ ID NO: 34; and (b) a $V_L$ which comprises a LC CDR1 of SEQ ID NO: 37, a LC CDR2 of SEQ ID NO: 39, and a LC CDR3 of SEQ ID NO: 41.

In some embodiments, the third antibody comprises a $V_H$ comprising SEQ ID NO: 75 or an amino acid sequence substantially identical thereto and a $V_L$ comprising SEQ ID NO: 76 or an amino acid sequence substantially identical thereto. Specifically, the third antibody includes a $V_H$ comprising an amino acid sequence has at least 80% (e.g. 82%, 84%, 85%, 86%, 88%, 90%, 92%, 94%, 95%, 96%, 98%, or 99%) identity to SEQ ID NO: 75, and a $V_L$ comprising an amino acid sequence has at least 80% (e.g. 82%, 84%, 85%, 86%, 88%, 90%, 92%, 94%, 95%, 96%, 98%, or 99%) identity to SEQ ID NO: 76. The third antibody also includes any recombinantly (engineered)-derived antibody encoded by the polynucleotide sequence encoding the relevant $V_H$ or $V_L$ amino acid sequences as described herein.

A functional variant of mAb22-1.5 (specific to DENV4) (also referred to "a fourth antibody specific for DENV4" as described herein) can comprise (a) a $V_H$ which comprises a HC CDR1 of SEQ ID NO: 44, a HC CDR2 of SEQ ID NO: 46, and a HC CDR3 of SEQ ID NO: 48; and (b) a $V_L$ which comprises a LC CDR1 of SEQ ID NO: 51, a LC CDR2 of SEQ ID NO: 53, and a LC CDR3 of SEQ ID NO: 55.

In some embodiments, the fourth antibody comprises a $V_H$ comprising SEQ ID NO: 77 or an amino acid sequence substantially identical thereto and a $V_L$ comprising SEQ ID NO: 78 or an amino acid sequence substantially identical thereto. Specifically, the fourth antibody includes a $V_H$ comprising an amino acid sequence has at least 80% (e.g. 82%, 84%, 85%, 86%, 88%, 90%, 92%, 94%, 95%, 96%, 98%, or 99%) identity to SEQ ID NO: 77, and a $V_L$ comprising an amino acid sequence has at least 80% (e.g. 82%, 84%, 85%, 86%, 88%, 90%, 92%, 94%, 95%, 96%, 98%, or 99%) identity to SEQ ID NO: 78. The fourth antibody also includes any recombinantly (engineered)-derived antibody encoded by the polynucleotide sequence encoding the relevant $V_H$ or $V_L$ amino acid sequences as described herein.

A functional variant of mAb82-1.1 (also referred to "a fifth antibody specific for DENV1, DENV2, DENV3, and DENV4" as described herein) can comprise (a) a $V_H$ which comprises a HC CDR1 of SEQ ID NO: 58, a HC CDR2 of SEQ ID NO: 60, and a HC CDR3 of SEQ ID NO: 62; and (b) a $V_L$ which comprises a LC CDR1 of SEQ ID NO: 65, a LC CDR2 of SEQ ID NO: 67, and a LC CDR3 of SEQ ID NO: 69.

In some embodiments, the fifth antibody comprises a $V_H$ comprising SEQ ID NO: 79 or an amino acid sequence substantially identical thereto and a $V_L$ comprising SEQ ID NO: 80 or an amino acid sequence substantially identical thereto. Specifically, the fourth antibody includes a $V_H$ comprising an amino acid sequence has at least 80% (e.g. 82%, 84%, 85%, 86%, 88%, 90%, 92%, 94%, 95%, 96%, 98%, or 99%) identity to SEQ ID NO: 79, and a $V_L$ comprising an amino acid sequence has at least 80% (e.g. 82%, 84%, 85%, 86%, 88%, 90%, 92%, 94%, 95%, 96%, 98%, or 99%) identity to SEQ ID NO: 80. The fourth antibody also includes any recombinantly (engineered)-derived antibody encoded by the polynucleotide sequence encoding the relevant $V_H$ or $V_L$ amino acid sequences as described herein.

The term "substantially identical" can mean that the relevant amino acid sequences (e.g., in FRs, CDRs, $V_H$, or $V_L$) of a variant differ insubstantially as compared with a reference antibody such that the variant has substantially similar binding activities (e.g., affinity, specificity, or both) and bioactivities relative to the reference antibody. Such a variant may include minor amino acid changes. It is understandable that a polypeptide may have a limited number of changes or modifications that may be made within a certain portion of the polypeptide irrelevant to its activity or function and still result in a variant with an acceptable level of equivalent or similar biological activity or function. In some examples, the amino acid residue changes are conservative amino acid substitution, which refers to the amino acid residue of a similar chemical structure to another amino acid residue and the polypeptide function, activity or other biological effect on the properties smaller or substantially no effect. Typically, relatively more substitutions can be made in FR regions, in contrast to CDR regions, as long as they do not adversely impact the binding function and bioactivities of the antibody (such as reducing the binding affinity by more than 50% as compared to the original antibody). In some embodiments, the sequence identity can be about 80%, 82%, 84%, 85%, 86%, 88%, 90%, 92%, 94%, 95%, 96%, 98%, or 99%, or higher, between the reference antibody and the variant. Variants can be prepared according to methods for altering polypeptide sequence known to one of ordinary skills in the art such as those found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989. For example, conservative substitutions of amino acids include substitutions made amongst amino acids within the following groups: (i) A, G; (ii) S, T; (iii) Q, N; (iv) E, D; (v) M, I, L, V; (vi) F, Y, W; and (vii) K, R, H.

The antibodies described herein may be animal antibodies (e.g., mouse-derived antibodies), chimeric antibodies (e.g., mouse-human chimeric antibodies), humanized antibodies, or human antibodies. The antibodies described herein may be monoclonal or polyclonal. A "monoclonal antibody" refers to a homogenous antibody population, and a "polyclonal antibody" refers to a heterogeneous antibody population. The antibodies described herein may also include their antigen-binding fragments e.g. a Fab fragment, a F(ab')2 fragment, a Fv fragment, a single chain Fv (scFv) and a (scFv)$_2$. The antibodies or their antigen-binding fragments can be prepared by methods known in the art.

III. Preparation of Antibodies

Numerous methods conventional in this art are available for obtaining antibodies or antigen-binding fragments thereof.

In some embodiments, the antibodies provided herein may be made by the conventional hybridoma technology. In general, a target antigen, e.g. a dengue virus NS1 protein, optionally coupled to a carrier protein, e.g. keyhole limpet hemocyanin (KLH), and/or mixed with an adjuvant, e.g complete Freund's adjuvant, may be used to immunize a host animal for generating antibodies binding to that antigen. Lymphocytes secreting monoclonal antibodies are harvested and fused with myeloma cells to produce hybridoma. Hybridoma clones formed in this manner are then screened to identify and select those that secrete the desired monoclonal antibodies.

In some embodiments, the antibodies provided herein may be prepared via recombinant technology. In related aspects, isolated nucleic acids that encode the disclosed amino acid sequences, together with vectors comprising such nucleic acids and host cells transformed or transfected with the nucleic acids, are also provided.

For examples, nucleic acids comprising nucleotide sequences encoding the heavy and light chain variable regions of such an antibody can be cloned into expression vectors (e.g., a bacterial vector such as an E. coli vector, a yeast vector, a viral vector, or a mammalian vector) via routine technology, and any of the vectors can be introduced into suitable cells (e.g., bacterial cells, yeast cells, plant cells, or mammalian cells) for expression of the antibodies. Examples of nucleotide sequences encoding the heavy and light chain variable regions of the antibodies as described herein are as shown in Table 3 below. Examples of mammalian host cell lines are human embryonic kidney line (293 cells), baby hamster kidney cells (BHK cells), Chinese hamster ovary cells (CHO cells), African green monkey kidney cells (VERO cells), and human liver cells (Hep G2 cells). The recombinant vectors for expression the antibodies described herein typically contain a nucleic acid encoding the antibody amino acid sequences operably linked to a promoter, either constitutive or inducible. Typical vectors contain transcription and translation terminators, initiation sequences, and promoters useful for regulation of the expression of the nucleic acid encoding the antibody. The vectors optionally contain selection markers for both prokaryotic and eukaryotic systems. In some examples, both the heavy and light chain coding sequences are included in the same expression vector. In other examples, each of the heavy and light chains of the antibody is cloned into an individual vector and produced separately, which can be then incubated under suitable conditions for antibody assembly.

The recombinant vectors for expression the antibodies described herein typically contain a nucleic acid encoding the antibody amino acid sequences operably linked to a promoter, either constitutive or inducible. The recombinant antibodies can be produced in prokaryotic or eukaryotic expression systems, such as bacteria, yeast, insect and mammalian cells. Typical vectors contain transcription and translation terminators, initiation sequences, and promoters useful for regulation of the expression of the nucleic acid encoding the antibody. The vectors optionally contain selection markers for both prokaryotic and eukaryotic systems. The antibody protein as produced can be further isolated or purified to obtain preparations that substantially homogeneous for further assays and applications. Suitable purification procedures, for example, may include fractionation on immunoaffinity or ion-exchange columns, ethanol precipitation, sodium dodecyl sulfate polyacrylamide gel electrophoresis (SDS-PAGE), high-performance liquid chromatography (HPLC), ammonium sulfate precipitation, and gel filtration.

When a full-length antibody is desired, coding sequences of any of the $V_H$ and $V_L$ chains described herein can be linked to the coding sequences of the Fc region of an immunoglobulin and the resultant gene encoding a full-length antibody heavy and light chains can be expressed and assembled in a suitable host cell, e.g., a plant cell, a mammalian cell, a yeast cell, or an insect cell.

Antigen-binding fragments can be prepared via routine methods. For example, F(ab')$_2$ fragments can be generated by pepsin digestion of an full-length antibody molecule, and Fab fragments that can be made by reducing the disulfide bridges of F(ab')$_2$ fragments. Alternatively, such fragments can also be prepared via recombinant technology by expressing the heavy and light chain fragments in suitable host cells and have them assembled to form the desired antigen-binding fragments either in vivo or in vitro. A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

IV. Use of Antibodies

The serotype-specific antibodies of the present invention are specific for respective dengue virus serotypes, and each of which does not react with any other closely related viruses such as other flavivirus e.g. Japanese encephalitis (JE) virus and Zika virus (ZIKV). The present invention thus provides a method employing any of the disclosed antibodies or any combination thereof that can be effectively employed to detect dengue virus in a sample.

In general, the method of the present invention comprises contacting the sample with any of the disclosed antibodies or any combination thereof and assaying binding of the antibody with said sample. Particularly, the binding of the antibody with said sample includes (i) binding of a first antibody to DENV1 NS1 and forming a $1^{st}$ antibody-DENV1 NS1 complex, (ii) binding of a second antibody to DENV2 NS1 and forming a $2^{nd}$ antibody-DENV2 NS1 complex, (iii) binding of a third antibody to DENV3 NS1 and forming a $3^{rd}$ antibody-DENV3 NS1 complex, and (iv) binding of a fourth antibody to DENV4 NS1 and forming a $4^{th}$ antibody-DENV4 NS1 complex. The method of the present invention further comprises determining the presence of absence of a particular serotype dengue virus based on the binding of the antibody with the sample, wherein (i) binding of a first antibody to DENV1 NS1 and forming a 1st antibody-DENV1 NS1 complex is an indicative of the presence of DENV1 in the sample, (ii) binding of a second antibody to DENV2 NS1 and forming a $2^{nd}$ antibody-DENV2 NS1 complex is an indicative of the presence of DENV2 in the sample, (iii) binding of a third antibody to DENV3 NS1 and forming a $3^{rd}$ antibody-DENV3 NS1 complex is an indicative of the presence of DENV3 in the sample, and (iv) binding of a fourth antibody to DENV4 NS1 and forming a 4th antibody-DENV4 NS1 complex is an indicative of the presence of DENV4 in the sample.

There are various assay formats known to those of ordinary skill in the art for using antibodies to detect an antigen or pathogen in a sample. These assays that use antibodies specific to target antigens/pathogens are generally called immunoassays. Examples of immunoassays include but are not limited to ELISA (enzyme-linked immunosorbent assay), RIA (radioimmunoassay), FIA (fluorescence immunoassay), LIA (luminescence immunoassay), or ILMA immunoluminometric assay. Such assays can be employed to detect the presence of dengue virus in biological samples including blood, serum, plasma, saliva, cerebrospinal fluid, urine, and other tissue specimens.

In certain embodiments, the assay is a sandwich assay.

In some embodiments, the assay is performed by first immobilizing a capture antibody on a solid support. The immobilized antibody is then incubated with the biological sample, and the dengue virus or its target antigen e.g. a NS1 polypeptide (if present in the sample) is allowed to bind to the antibody, to form an antibody-virus/antigen complex or conjugate. Unbound sample can then be removed by washing the solid support with an appropriate buffer, such as PBS containing 0.05% Tween, and a detection antibody that can bind to the immobilized antibody-virus/antigen complex and comprises a detectable label is added to the solid support. Specifically, the capture antibody and the detection antibody need to bind to the virus/antigen at different epitopes such that the virus/antigen can be "sandwiched" between the two antibodies. Preferred detectable labels include an enzymatic label (such as horseradish peroxidase), a fluorescent label, a metal label and a radio label. Some particular examples of detectable labels include gold nanoparticles, colored latex beads, magnetic particles, carbon nanoparticles and selenium nanoparticles. The detection antibody is incubated with the immobilized antibody-virus/antigen complex for a period of time sufficient to detect the bound virus/antigen. Unbound detection antibody is then removed and bound detection antibody is detected based on the detectable label. For example, an enzymatic label may be generally be detected by the addition of substrate, followed by spectroscopic or other analysis of the reaction products.

To determine the presence or absence of target dengue virus in the sample, the signal detected from the detectable label bound to the solid support is generally compared to a signal that corresponds to a cut-off value. This cut-off value is typically the average mean signal obtained when the immobilized antibody is incubated with samples from an uninfected subject. In general, a sample generating a signal that is higher than the cut-off value is considered positive for the presence of dengue virus in the sample.

The serotype-specific antibodies of the present invention can be used as capture or detection antibodies, paired with a partner antibody, to form an antibody pair to perform a sandwich assay. A partner antibody as described herein needs to be able to also bind to the target virus/antigen but at a different epitope than any of the serotype-specific antibodies of the present invention as used in the pair for performing a sandwich assay. In some embodiments, a partner antibody for performing a sandwich assay can be a different "serotype specific" antibody to dengue virus other than any of those described herein (i.e. the first antibody, the second antibody, the third antibody and the forth antibody)

which also is capable of biding to the respective serotype of dengue virus but at a different epitope. In some embodiments, a partner antibody can be a "serotype cross-reactive" antibody, either a polyclonal or monoclonal antibody, which can recognize all dengue virus serotypes but at a different epitope than any of the serotype-specific antibodies of the present invention does. One certain example of such cross-reactive antibody is the fifth antibody (e.g. mAb82-1.1) which is cross-reactive to at least four serotypes of dengue virus and recognizes a separate epitope than any of the serotype-specific antibodies of the present invention does, thus forming a matched pair therewith to perform a sandwich assay.

In some embodiments, the method of the present invention for detecting dengue virus in a sample comprises (i) contacting the sample with a cross-reactive antibody specific for a dengue NS1 polypeptide (for four serotypes) (e.g. a fifth antibody specific to DENV1 NS1, DENV2 NS1, DENV3 NS1 and DENV4 NS1), as a capture antibody, to form a cross-reactive antibody-NS1 (any serotypes) complex;

(ii) contacting the cross-reactive antibody-NS1 polypeptide (any serotypes) complex with a serotype-specific monoclonal antibody as described herein (e.g. a first antibody specific to DENV1 NS1, a second antibody specific to DENV2 NS1, a third antibody specific to DENV3 NS1, or a fourth antibody specific to DENV4 NS1), as a detection antibody, to form a cross-reactive antibody-NS1 (any serotypes)-serotype-specific monoclonal antibody complex; and (iii) detecting the presence of the cross-reactive antibody-NS1 (any serotypes)-serotype-specific monoclonal antibody complex, thereby detecting the presence of respective serotype dengue virus in the sample.

In some embodiments, the method of the present invention for detecting dengue virus in a sample comprises (i) contacting the sample with a serotype-specific monoclonal antibody as described herein (e.g. a first antibody specific to DENV1 NS1, a second antibody specific to DENV2 NS1, a third antibody specific to DENV3 NS1, or a fourth antibody specific to DENV4 NS1), as a capture antibody, to form a monoclonal antibody-serotype specific NS1 complex;

(ii) contacting the monoclonal antibody-respective serotype dengue virus complex with a cross-reactive antibody specific for a dengue NS1 polypeptide (for four serotypes) (e.g. a fifth antibody specific to DENV2 NS1, DENV2 NS1, DENV3 NS1 and DENV4 NS1), as a detection antibody, to form a monoclonal antibody-serotype specific NS1-cross-reactive antibody complex; and (iii) detecting the presence of the serotype-specific monoclonal antibody-NS1-cross-reactive antibody complex, thereby detecting the presence of respective serotype dengue virus in the sample.

In one example, the method of the present invention is performed in an ELISA sandwich assay. In this assay, the capture antibody is coated onto ELISA plates. After blocking, the plates are incubated with the biological sample, washed and then incubated with a detection antibody. For example, the capture antibody is a polyclonal or monoclonal, cross-reactive antibody specific for a dengue NS1 polypeptide (any serotypes), and the detection antibody is a first antibody specific to DENV1 NS1, a second antibody specific to DENV2 NS1, a third antibody specific to DENV3 NS1, or a fourth antibody specific to DENV4 NS1, or any combination thereof, as described herein, and the plate is developed using a ELISA colorimetric TMB reagent.

In another example, the method of the present invention is performed in a flow-through or lateral flow format. In this assay, the detection antibody with a detectable label such as a colorimetric label (e.g. colloidal gold) is immobilized to a membrane such as nitrocellulose (as a strip). A biological sample suspected of containing said dengue virus is applied to the membrane to which the detection antibody is present. The biological sample migrates along the membrane through a region containing the detection antibody wherein the detection antibody binds to the NS1 of the dengue virus if present in the biological sample. The complex of the detection body with its bound antigen then migrates to the test area where a capture antibody is immobilized and also binds the NS1 of the dengue virus, thereby forming a sandwich of the detection antibody, antigen and capture antibody. Concentration/aggregation of detection antibody at the test (capture) area indicates the presence of specific dengue NS1 in the sample. Such tests can typically be performed with a very small amount of biological sample.

In a related aspect, the present invention also provides a kit for performing the method of the invention, which comprises any of the antibody or its combination thereof as described herein. The kit can further comprise instructions for using the kit to detect the dengue virus in a sample.

In some embodiments, the immunoassay is in a sandwich format.

In particular, the kit comprises a pair of a dengue virus serotype-specific antibody selected from the group consisting of a first antibody specific to DENV1 NS1, a second antibody specific to DENV2 NS1, a third antibody specific to DENV3 NS1, and a forth antibody specific to DENV4 NS1, and any combination thereof, each antibody paired with a partner antibody for performing a sandwich assay In certain embodiments, at least one of the serotype-specific antibodies is performed as a capture antibody, paired with a partner antibody as a detection antibody.

In other embodiments, at least one of the serotype-specific antibodies is performed as a detection antibody, paired with a partner antibody as a capture antibody.

As a detection antibody, the antibody can comprises a detectable label such as an enzymatic label, a fluorescent label, a metal label and a radio label.

In some examples, in a lateral flow format, the kit comprises an assay strip (e.g. a nitrocellulose membrane); a detection antibody may be bound to a reaction zone of the strip, and a capture antibody may be bound in a test zone of the strip. The strip also contains a sample pad where a body fluid sample is placed to and then the sample migrates towards an opposite end of the strip by capillary action, through which the sample first engages the detection antibody in the reaction zone where the antigen in the sample bind to the detection antibody forming an antigen-detection antibody complex and then the antigen-detection antibody complex engages the capture antibody in the test (capture) zone. Using colloidal gold as the detectable label of the detection antibody, for example, concentration/aggregation of detection label at the test (capture) area reveals red color, indicating the presence of specific antigen in the sample. Alternatively, the test zone may have a chromogenic substrate and when the antigen-detection antibody complex engage the capture antibody, the chromogenic substrate is converted to a visible colored product.

In some examples, in an ELISA format, the kit comprises a microtiter plate with wells to which a capture antibody has been immobilized; a solution containing a detection antibody; and a color developing reagent.

Particularly, the kit may further comprise additional reagents or buffers, a medical device for collecting a biological sample form a subject, and/or a container for holding and/or storing the sample.

In further embodiments, the present invention provides compositions comprising one or more antibodies as described herein and a pharmaceutically acceptable carrier.

In some embodiments, the composition of the present invention is a pharmaceutical composition for use in treatment of dengue virus disease.

In some embodiments, the composition of the present invention is a diagnostic composition for use in diagnosis of dengue virus disease.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

Examples 1.1 Viral Strains

Dengue viral strains DENV1 Hawaii, DENV2 16681, DENV3 H87, and DENV4 H241 were propagated in C6/36 *Aedes albopictus* in RPMI 1640 medium supplemented with 2% FBS and incubated at 28° C. until cytopathic effects were observed. As a control, the viral strain JEV SA14-14-2 was propagated in BHK-21 cells in RPMI 1640 medium containing 2% FBS. The titers of each virus were determined via plaque assays in which BHK-21 cells were inoculated.

1.2 Preparation of NS1 Proteins

Cell culture supernatants of Vero cells infected with viruses (DENV1 Hawaii, DENV2 16681, DENV3 H87, and DENV4 H241) were harvested after five days and inactivated by UV irradiation. To purify the soluble form of NS1 proteins in cell culture supernatants, we performed immunoaffinity chromatography column according to manufacturer's instructions. For this, anti-NS1 monoclonal antibodies (for all serotype) that had been immobilized onto a HiTrap™ NHS-activated HP column (GE Healthcare, Uppsala, Sweden) were used to purify NS1 proteins from each of the dengue serotypes. Equilibrate the column with 5 volumes of PBS, viral cell culture supernatants were passed over the immunoaffinity column, washing out unbound proteins with ten volumes of PBS and bound NS1 were eluted using glycine solution with a pH of 2.8, then buffered to neutral pH. The purified DENV NS1 proteins were then detected by Western blot analysis, and NS1 protein concentrations were determined using a Pierce BCA protein assay kit (Thermo Fisher Scientific, Illinois, USA).

1.3 Generation and Characterization of Serotype-Specific mAbs Against DENV1-4 NS1

All experiments used BALB/c mice that were purchased from the National Laboratory Animal Center and maintained at the Institute of Preventative Medicine's animal housing facility. Experiments using animals were licensed by the Association for Assessment and Accreditation of Laboratory Animal Care International (IACUC no AN-104-12, AN-105-05). Four-week-old BALB/c mice were immunized i.p. with 15 μg of immunoaffinity-purified NS1 proteins in complete Freund's adjuvant for the first inoculation and the mice were then immunized against their respective serotypes with 15 μg of NS1 proteins in incomplete Freund's adjuvant for the subsequent boosting. DENV-specific antisera were obtained from the mice after consecutive challenge. Briefly, spleen of an immunized mouse was removed. Splenocytes were fused with NS1/1-Ab4-1 myeloma cells to generate hybridoma cells, which were selected according to standard procedures (Kohler & Milstein, 1975). After fused cells were wash twice with RPMI then mixed in a 15 ml conical tube and 1 ml 50% (w/v) PEG 1500 (Roche, Penzberg, Germany) was added over 1 min with gentle stirring. The mixture was diluted by slow (1 min) addition of 1 ml RPMI, twice, followed by the slow addition (2 min) of 8 ml serum-free RPMI. The mixture was then centrifuged at 400 g for 5 min. The fused cell pellet was re-suspended in RPMI supplemented with 20% FBS, HAT medium (Life technologies, Burlington, ONT Canada) and HFCS solution (Roche, Mannhein, Germany). Next, 200 μl per well of the resuspension mixture was distributed in 96-well plates. The hybridoma cell lines that secreted specific antibodies against NS1 were identified by indirect ELISA (using purified DENV NS1 as the coating antigen for each serotype). Single clone cells were generated by limiting dilution. Western blotting of lysates from C6/36 cells infected with DENVs was performed to determine (a) the specificity of anti-NS1 mAbs and (b) whether the epitopes recognized by the antibodies were conformation or linear. The mAbs were isotyped using a commercially available mouse monoclonal antibody isotyping kit (IsoStrip™, Roche, Mannheim, Germany). The hybridoma cells were injected into pristane-primed BALB/c mice for ascitic fluid production. mAbs were then purified from ascitic fluids using a protein G-sepharose column (HiTrap protein G, GE Healthcare, Uppsala, Sweden) according to the manufacturer's instructions.

1.4 IMP Conjugation

To conjugate mAbs with HRP (Innova Biosciences, Cambridge, UK), 100 μg of HRP and a 20 μl aliquot of modifier reagent were mixed with 200 μl of 1 mg/ml mAb. After incubating the mixture for 3 hours at room temperature (20-25° C.), the reaction was stopped with a 20 μl aliquot of quencher. Following incubation for an additional 30 min at room temperature, 260 μl of glycerol was added, and the final solution was stored at −20° C. The final concentration of mAb-HRP was 400 μg/ml.

1.5 Development of Four Serotype-Specific NS1 Capture ELISAs

Several serotype-specific and highly reactive mAbs were selected based on the characteristics of anti-NS1 mAbs. The serotype-specific antibodies in a capture ELISA format of the four serotype-specific mAbs were tested by for compatibility with serotype-cross-reactive mAbs. To determine the best combinations for the capture ELISA with respect to assay sensitivity, the serotype-specific mAbs and serotype-cross-reactive mAbs were used as either capture or detection antibodies. Specifically, serotype-cross-reactive mAbs were selected as a capture antibody, and optimal pairing to the respective four serotype-specific mAbs (mAb12-4.1, mAb33-7.1, mAb43-1.3, and mAb22-1.5) as detection antibodies was determined, the Dengue four serotype NS1 ELISA was assembled, as shown in FIG. 1A, FIG. 1B, FIG. 2A and FIG. 2B. The most appropriate experimental condition such as coating concentration and the dilution of mAb-HRP were determined by checkerboard titration. Microwell plates (Costar Corning Inc., Corning, N.Y.) were coated with 100 μl of 10 μg/ml of capture cross-reactive mAb and incubated overnight at 4° C. Wells were subsequently blocked with blocking buffer (PBS, 0.05% Tween, 5% skim milk) for 1 h at 37° C. and washed with wash buffer (PBS, 0.05% Tween). Viral culture supernatant or NS1 proteins were then serially diluted with blocking buffer and incubated for 1 h at 37° C. After the plates were washed, 100 μl of 0.8 μg/ml of serotype-specific mAb-HRP was added, and the plates were incubated for 1 h at 37° C. Following this, the plates were washed again, 100 μl of TMB reagent was added, and the plates were incubated for 10 min at room temperature. The reaction was then stopped with 1 N sulfuric acid, and the absorbance was read at 450 nm using a microplate autoreader.

1.6 Clinical Samples

A total of 146 clinical serum samples were used in this study; 85 samples comprised confirmed dengue cases that had been reported to the Centers for Disease Control, Department of Health, Taipei, and 61 samples were collected from three hospitals during 2016-2017 (Kaohsiung Armed Forces General Hospital, Zuoying Branch of Kaohsiung Armed Forces General Hospital, and Tangshan Branch of Kaohsiung Armed Forces General Hospital). All clinical serum samples were collected during the acute phase (1-7 days after onset of illness) and tested with serotype-specific one-step SYBR green I real time RT-PCR, dengue virus specific IgM/IgG capture ELISA and commercially available Platelia Dengue NS1 Ag ELISA kit (Bio-Rad, Marnes-la-Coquette, France). The study protocol was approved by the Kaohsiung Armed Forces General Hospital Institutional Review Board (IRB no. KAFGH 104-048).

1.7 Testing Clinical Sera for NS1 Using Serotype-Specific NS1 Capture ELISA

Microwell plates were coated with 100 μl of 10 μg/ml of a cross-reactive mAb and incubated overnight at 4° C. Wells were subsequently blocked with blocking buffer (PBS, 0.05% Tween, 5% skim milk) and incubated with 50 μl of sera diluted in blocking buffer at a 1:1 ratio for 1 h at 37° C. The plates were then washed four times with 0.05% PBS/T, incubated with 100μl of 0.8 μg/ml of serotype-specific mAb-HRP (mAb12-4.1, mAb33-1.7, mAb43-1.3, and mAb22-1.5) for 1 h at 37° C., and washed four times again. Subsequent steps involved in the testing of clinical sera were as described in the previous section. Normal human serum samples (Sigma-Aldrich, Saint Louis, USA) were used as a negative control. For each serotype, samples that exceeded the reference cut-off value, calculated as the two-fold mean of the negative control, were considered positive in the NS1 capture ELISA.

1.8 Detection of NS1 Antigens by a Commercially Available Platelia Dengue NS1 Ag ELISA Kit (Bio-Rad, Marnes-la-Coquette, France)

DENV NS1 proteins were detected in clinical serum samples using a commercially available Platelia Dengue NS1 Ag ELISA kit (Bio-Rad, Marnes-la-Coquette, France) according to the manufacturer's instructions. Briefly, dilutions of positive, negative, calibration, and samples were incubated on well plates with HRP-conjugated mAbs for 90 min at 37° C. After washing the plates six times, 160 μl of TMB was added into each well, and plates were incubated for 30 min at room temperature away from light. The enzymic reaction was stopped by adding 100 μl of stop solution, and optical densities were measured at OD 450/620 nm.

1.9 Reproducibility

A total of 58 DENV positive serum samples (16 serum samples for DENV1, 17 serum samples for DENV2, 16 serum samples for DENV3, and 9 serum samples for DENV4) and 50 negative serum samples were tested by the four-serotype NS1 capture ELISAs by a second operator on a different day.

1.10 Statistical Analysis

Diagnosis accuracy, sensitivity, specificity, and the corresponding 95% confidence intervals (CI95) for each ELISA were performed using GraphPad Prism version 6.0 (GraphPad software, San Diego, Calif.), and the significance level was set at a P value of <0.05.

1.11 Preparation of Colloidal Gold Probe

Colloid gold 35±5 nm (TANBead NanoGold-40, Taiwan Advanced Nanotech) was used for conjugation of IgG. The colloid gold solution (1% w/v) was adjusted pH with 0.2 N NaOH and anti-dengue NS1 mAb82-1.1 (in PBS, PH 7.4) was added to pH-adjusted colloid gold solution. The most appropriate pH value for each serotype conjugation were PH 7.8 for D1 strip; PH 7.4 for D2, D3, and D4 strip. The optimized antibody concentration for conjugation was 1 μg/strip. The antibody/colloid gold mixture was gently mixed for 90 min, blocked by 2% BSA solution for 30 min and centrifuged at 7000 rpm for 15 min. After centrifugation and wash once by 2% BSA (20 mM Tris/HCl buffer [pH7.2] containing 2% [w/v] BSA), the gold pellets were suspended in 2% BSA. Make this anti-gengue NS1 mAb82-1.1 coated colloidal gold probe to release pad and dried then stored at 4° C. over night.

1.12 Preparation of Lateral Flow Test Strips

The control lines were prepared as follows: 0.2 (for D1, D3, and D4) to 0.32 (for D2) μg/strip of goat anti mouse IgG (Jackson ImmunoResearch, PA, USA). Test lines (capture antibodies) were prepared as follows: mAb12-4.1, mAb43-1.3, mAb22-1.5 working strength were 0.75 μg/strip (for D1, D3, D4 strip) in PBS (pH 7.4), and mAb33-7.1 working strength was 0.8 μg/strip (for D2 strip) in PBS (pH 7.4) were separately applied near to the top end of a cellulose acetate supported strip of nitrocellulose membrane (Pore size: 12 µm-diameter) and dried for 1 h at room temperature. After treatment of components, the Dengue serotype NS1 lateral flow test device was assembled.

1.13 Assay of NS1 Antigens on Strip and the Detection Sensitivity

The assay was carried out by applying a sample (50₁11) of the appropriate test DENV NS1 protein solution and 500 running buffer (0.1% Tween-20/0.85% NaCl) to the sample pad of the device. The combined solution of test DENY NS1 and detection reagent rose up the membrane and colloidal gold was deposited at the site of the solid-phase antibody after 20 min at room temperature.

1.14 Cross-Reactivity of DENY Serotype NS1 Strip

Cell culture supernatants of Vero cells infected with viruses (DENV1 Hawaii, DENV2 16681, DENV3 H87, DENV4 H241, JEV, and ZIKV) were assayed by DENV serotype NS1 strip for evaluating cross-reactivity.

1.15 Sequence Analysis of Monoclonal Antibodies Variable Domains

The hybridoma cells from hybridomas 12-4.1, 33-7.1, 43-1.3, 22-1.5, and 82-1.1. Total RNA was isolated from hybridoma cell lines using RNeasy mini kit (Qiagen, Valencia, Ca. USA) according to manufacturer's protocol, followed by reverse transcription using oligo dT primer to generate cDNA. The heavy chain and light variable chains of the antibody are amplified using PCR and confirmed the sequence is functional variable domain. The VH and VL genes of four hybridoma cells, see attached file for sequence.

2. Results 2.1 Generation and Characterization of mAbs Against DENV

NS1 proteins from various serotypes of DENV were prepared and injected into the BALB/c mice for immunization. Spleen was removed from the immunized mice and splenocytes were isolated and fused with myeloma cells to generate hybridoma cells. The hybridoma cell lines that secreted specific antibodies against NS1 were identified by ELISA using purified DENV NS1 as the coating antigen for each serotype. In addition, western blotting of lysates from C6/36 cells infected with DENVs was performed to determine (a) the specificity of anti-NS1 mAbs and (b) whether the epitopes recognized by the antibodies were conformation or linear. Further, the mAbs were isotyped using a commercial kit.

TABLE 2

Characterization of mAb reactions with NS1 proteins of DENV serotypes (D1-4)

| Hybridoma cell strain | Isotype | Type of epitope | Reactivity of the four DENV serotypes (D1-4) | | | | | | | | Specificity |
|---|---|---|---|---|---|---|---|---|---|---|---|
| | | | Western blot[a] | | | | ELISA[b] | | | | |
| | | | D1 | D2 | D3 | D4 | D1 | D2 | D3 | D4 | |
| mAb12-4.1 | IgG1,κ | conformational | + | − | − | − | + | − | − | − | NS1 |
| mAb33-7.1 | IgG1,κ | conformational | − | + | − | − | − | + | − | − | NS1 |
| mAb43-1.3 | IgG1,κ | conformational | − | − | + | − | − | − | + | − | NS1 |
| mAb22-1.5 | IgG1,κ | conformational | − | − | − | + | − | − | − | + | NS1 |
| mAb82-1.1 | IgG1,κ | linear | + | + | + | + | + | + | + | + | NS1 |

[a]The lysates of C6/36 cells infected with different dengue virus serotypes were treated with SDS-PAGE sample buffer and blotted with each mAb.
[b]Different NS1 antigens were immunoaffinity-purified from cell culture supernatants of Vero cells infected with different serotypes of DENV. Microwell plates were coated with specific NS1 antigens and reacted with each mAb.

As shown in Table 2, the 1st to 4th clones, 12-4.1, 33-7.1, 43-1.3, and 22-1.5, are serotype specific to DENV1, DENV2, DENV3 and DENV4, respectively, while the 5th clone, mAb82-1.1, is cross-reactive to DENV1, DENV2, DENV3 and DENV4.

The amino acid sequences of the four serotype-specific mAbs (12-4.1, 33-7.1, 43-1.3, and 22-1.5) and the cross-reactive mAb (82-1.1), including the complementary determining regions 1-3 (CDR 1-3) and framework regions 1-4 (FW1-4) for both the VH and VL domains and corresponding nucleic acid sequences were determined and provided in Table 3 below.

TABLE 3

The amino acid sequences of the four serotype-specific mAbs (12-4.1, 33-7.1, 43-1.3, and 22-1.5) and the cross-reactive mAb (82-1.1) and corresponding nucleic acid sequences.

| $V_H$ domain | FW1 | CDR1 | FW2 | CDR2 |
|---|---|---|---|---|
| 12-4.1 | EVKLQESGAELAKP GASVKMSCRAS (SEQ ID NO: 1) | GYTFTSYWIH (SEQ ID NO: 2) | WVKERPGQGLEWIG (SEQ ID NO: 3) | YITPNTGYNENSQKFRG (SEQ ID NO: 4) |
| 33-7.1 | EVQLQESGAELAKP GASVKMSCKAS (SEQ ID NO: 15) | GYTFTSYWMH (SEQ ID NO: 16) | WVKQRPGQVLEWIG (SEQ ID NO: 17) | YINPNTGFTEYSQKFKD (SEQ ID NO: 18) |

TABLE 3-continued

The amino acid sequences of the four serotype-specific mAbs
(12-4.1, 33-7.1, 43-1.3, and 22-1.5) and the cross-reactive mAb
(82-1.1) and corresponding nucleic acid sequences.

| | | | |
|---|---|---|---|
| 43-1.3 GELQESGPQVVRPG<br>TSVKISCKAS<br>(SEQ ID NO: 29) | GYSFSNYWMH<br>(SEQ ID NO: 30) | WVKQRPGQGLEWIG<br>(SEQ ID NO: 31) | VIDPSDSETRLNQKFKD<br>(SEQ ID NO: 32) |
| 22-1.5 EVQLQQSGPELVKP<br>GASVKISCKAS<br>(SEQ ID NO: 43) | GYTFTDYNIH<br>(SEQ ID NO: 44) | WVKQSPGKSLEWIG<br>(SEQ ID NO: 45) | YIYPDNGDTGYNQIFKN<br>(SEQ ID NO: 46) |
| 82-1.2 EVQLQQSGGGLVQP<br>GGSLKLSCAAS<br>(SEQ ID NO: 57) | GFTFSNYDMS<br>(SEQ ID NO: 58) | WIRQTPDKRLEMVA<br>(SEQ ID NO: 59) | AINSNGGSTYYPDSVKG<br>(SEQ ID NO: 60) |

| V<sub>H</sub> domain | FW3 | CDR3 | FW4 |
|---|---|---|---|
| 12-4.1 | KATLTADKSSNTAY<br>MQLSSLTSEDSAVYF<br>CVR<br>(SEQ ID NO: 5) | RTYEGYLDV<br>(SEQ ID NO: 6) | WGAGTTVTVSS<br>(SEQ ID NO: 7) |
| 33-7.1 | KATLTAVKSSSTAYIQ<br>LTSLTSDDSAVYYCA<br>R<br>(SEQ ID NO: 19) | ENYRYDGAMDY<br>(SEQ ID NO: 20) | WGQGTSVTVSS<br>(SEQ ID NO: 21) |
| 43-1.3 | KATLTVDKSSSTAYM<br>QLSSPTSEDSAIYYC<br>AR<br>(SEQ ID NO: 33) | SQFGLRFAY<br>(SEQ ID NO:34) | WGQGTLVTVSA<br>(SEQ ID NO: 35) |
| 22-1.5 | KATLTVDTSSSAAY<br>MELRSLTSEDSAVYY<br>CVR<br>(SEQ ID NO:47) | RVLLDS<br>(SEQ ID NO: 48) | WGQGTSVTVSS<br>(SEQ ID NO: 49) |
| 82-1.2 | RFTISRDKAKNTLYL<br>QMSSLKSEDTAMYY<br>CAS<br>(SEQ ID NO:61) | PNGYGAMDY<br>(SEQ ID NO: 62) | WGQGTSVTVSS<br>(SEQ ID NO: 63) |

| VL domain | FW1 | CDR1 | FW2 | CDR2 |
|---|---|---|---|---|
| 12-4.1 | DIVMTQTPLSLPVSL<br>GDQAS1SC<br>(SEQ ID NO: 8) | RSSQNLVHNNGNT<br>YLE<br>(SEQ ID NO: 9) | WYLQKPGQSPKLLIY<br>(SEQ ID NO: 10) | KVSNRLS<br>(SEQ ID NO: 11) |
| 33-7.1 | DIVLTQSPALMAAFP<br>GDRVT1TC<br>(SEQ ID NO: 22) | SVSSSVSSSNLH<br>(SEQ ID NO: 23) | WYQQKSETSPKPWIY<br>(SEQ ID NO: 24) | GTSTLAS<br>(SEQ ID NO: 25) |
| 43-1.3 | DIVMTQSPSSMTVTA<br>GEKVTMSC<br>(SEQ ID NO: 36) | QSSQSLFNSGTQKN<br>YLT<br>(SEQ ID NO: 37) | WYQQKPGQPPKLLIS<br>(SEQ ID NO: 38) | WASTRDS<br>(SEQ ID NO: 39) |
| 22-1.5 | DIQMTQTTSsLSAsL<br>GDRVTISC<br>(SEQ ID NO: 50) | SASQDINNFLN<br>(SEQ ID NO: 51) | WYQQKPDGTIKLLIY<br>(SEQ ID NO: 52) | YTSSLQS<br>(SEQ ID NO: 53) |
| 82-1.2 | DIVITQTPLTLSVTIG<br>QPASISC<br>(SEQ ID NO: 64) | KSRQSLLDSDGKTY<br>LN<br>(SEQ ID NO: 65) | WLLQRPGESPKLLIY<br>(SEQ ID NO: 66) | LVSKLDS<br>(SEQ ID NO: 67) |

| VL domain | FW3 | CDR3 | FW4 |
|---|---|---|---|
| 12-4.1 | GVPDRFSGSGSGTDF<br>TLNISRVEAEDLG1Y<br>YC<br>(SEQ ID NO: 12) | FQASHVPRT<br>(SEQ ID NO: 13) | FGGGTKLEIKR<br>(SEQ ID NO: 14) |
| 33-7.1 | GVPVRFSGSGSGTSY<br>SLTISSMEAEDAATY<br>YC<br>(SEQ ID NO: 26) | QQWSSYPLT<br>(SEQ ID NO:27) | FGAGTKLELKR<br>(SEQ ID NO: 28) |

TABLE 3-continued

The amino acid sequences of the four serotype-specific mAbs
(12-4.1, 33-7.1, 43-1.3, and 22-1.5) and the cross-reactive mAb
(82-1.1) and corresponding nucleic acid sequences.

| | | | |
|---|---|---|---|
| 43-1.3 | GVPDRFTGSGSGTD<br>FTLTINGVQAEDLAV<br>YFC<br>(SEQ ID NO: 40) | QNDYDSPYT<br>(SEQ ID NO: 41) | FGGGTKLEIKR<br>(SEQ ID NO: 42) |
| 22-1.5 | GVPSRFSGSGSGTDY<br>SLTISNLEPEDIATYY<br>C<br>(SEQ ID NO: 54) | QQYSKLPRT<br>(SEQ ID NO: 55) | FGGGTKLEIKR<br>(SEQ ID NO: 56) |
| 82-1.2 | GVPDRFTGSGSGTD<br>FTLKISRVEAEDLGV<br>YYC<br>(SEQ ID NO: 68) | LQATHFPWT<br>(SEQ ID NO:69) | FGGGTKLEIKRA<br>(SEQ ID NO: 70) |

Full-length amino acid sequences of heavy chain and light chain

| | |
|---|---|
| 12-4.1 heavy chain | EVKLQESGAELAKPGASVKMSCRASGYTFTSYWIHWVKERPGQG<br>LEWIGYITPNTGYNENSQKFRGKATLTADKSSNTAYMQLSSLTS<br>EDSAVYFCVRRTYEGYLDVWGAGTTVTVSS (SEQ ID NO:71) |
| light chain | DIVMTQTPLSLPVSLGDQASISCRSSQNLVHNNGNTYLEWYLQK<br>PGQSPKLLIYKVSNRLSGVPDRFSGSGSGTDFTLNISRVEAEDL<br>GIYYCFQASHVPRTFGGGTKLEIKR (SEQ ID NO: 72) |
| 33-7.1 heavy chain | EVQLQESGAELAKPGASVKMSCKASGYTFTSYWMHWVKQRPGQV<br>LEWIGYINPNTGFTEYSQKFKDKATLTAVKSSSTAYIQLTSLTS<br>DDSAVYYCARENYRYDGAMDYWGQGTSVTVSS (SEQ ID NO: 73) |
| light chain | DIVLTQSPALMAAFPGDRVTITCSVSSSVSSSNLHWYQQKSETS<br>PKPWIYGTSTLASGVPVRFSGSGSGTSYSLTISSMEAEDAATYY<br>CQQWSSYPLTFGAGTKLELKR (SEQ ID NO: 74) |
| 43-1.3 heavy chain | GELQESGPQVVRPGTSVKISCKASGYSFSNYWMHWVKQRPGQGL<br>EWIGVIDPSDSETRLNQKFKDKATLTVDKSSSTAYMQLSSPTSE<br>DSAIYYCARSQFGLRFAYWGQGTLVTVSA (SEQ ID NO: 75) |
| light chain | DIVMTQSPSSMTVTAGEKVTMSCQSSQSLFNSGTQKNYLTWYQQ<br>KPGQPPKLLISWASTRDSGVPDRFTGSGSGTDFTLTINGVQAED<br>LAVYFCQNDYDSPYTFGGGTKLEIKR (SEQ ID NO: 76) |
| 22-1.5 heavy chain | EVQLQQSGPELVKPGASVKISCKASGYTFTDYNIHWVKQSPGKS<br>LEWIGYIYPDNGDTGYNQIFKNKATLTVDTSSSAAYMELRSLTS<br>EDSAVYYCVRRVLLDSWGQGTSVTVSS (SEQ ID NO: 77) |
| light chain | DIQMTQTTSSLSASLGDRVTISCSASQDINNFLNWYQQKPDGTI<br>KLLIYYTSSLQSGVPSRFSGSGSGTDYSLTISNLEPEDIATYYC<br>QQYSKLPRTFGGGTKLEIKR (SEQ ID NO: 78) |
| 82-1.2 heavy chain | EVQLQQSGGGLVQPGGSLKLSCAASGFTESNYDMSWIRQTPDKR<br>LEMVAAINSNGGSTYYPDSVKGRFTISRDKAKNTLYLQMSSLKS<br>EDTAMYYCASPNGYGAMDYWGQGTSVTVSS (SEQ ID NO: 79) |
| light chain | DIVITQTPLTLSVTIGQPASISCKSRQSLLDSDGKTYLNWLLQR<br>PGESPKLLIYLVSKLDSGVPDRFTGSGSGTDFTLKISRVEAEDL<br>GVYYCLQATHFEWTEGGGTKLEIKRA (SEQ ID NO: 80) |

Nucleotide sequence

| | |
|---|---|
| 12-4.1 heavy chain | GAGGTCAAACTGCAGGAGTCTGGGGCTGAACTGGCAAAACCTGGGGCCTC<br>AGTGAAGATGTCCTGCAGGGCTTCTGGCTACACCTTTACCAGCTATTGGA<br>TACACTGGGTGAAAGAGAGGCCTGGACAGGGTCTGGAATGGATTGGATAC<br>ATTACTCCTAATACAGGTTATAATGAGAACAGTCAGAAGTTCAGGGGCAA<br>GGCCACATTGACTGCAGACAAATCCTCCAACACAGCTTATATGCAACTAA<br>GCAGCCTGACATCTGAGGACTCTGCAGTCTATTTCTGTGTAAGAAGGACG<br>TATGAGGGGTACCTCGATGTCTGGGGCGCAGGGACCACGGTCACCGTCTC<br>CTCA (SEQ ID NO: 81) |
| light chain | GACATTGTGATGACCCAAACTCCACTCTCCCTGCCTGTCAGTCTTGGAGA<br>TCAAGCCTCCATCTCTTGCAGATCTAGTCAGAACCTTGTACATAATAATG<br>GAAACACCTATTTAGAGTGGTACCTGCAGAAACCAGGCCAGTCTCCAAAG<br>CTCCTGATCTACAAAGTTTCCAACCGATTGTCTGGGGTCCCAGACAGGTT<br>CAGTGGCAGTGGATCCGGGACAGACTTCACACTCAATATCAGCAGAGTGG<br>AGGCTGAGGATCTGGGAATTTATTACTGCTTTCAGGCTTCACATGTTCCT<br>CGGACGTTCGGTGGAGGCACCAAGCTGGAAATCAAACGG (SEQ ID<br>NO: 82) |

TABLE 3-continued

The amino acid sequences of the four serotype-specific mAbs
(12-4.1, 33-7.1, 43-1.3, and 22-1.5) and the cross-reactive mAb
(82-1.1) and corresponding nucleic acid sequences.

| | |
|---|---|
| 33-7A heavy chain | GAGGTGCAGCTGCAGGAGTCAGGGGCTGAACTGGCAAAACCTGGGGCCTC<br>AGTGAAGATGTCCTGCAAGGCTTCTGGCTACACCTTTACTAGCTACTGGA<br>TGCACTGGGTAAAACAGAGGCCTGGACAGGTTCTGGAATGGATTGGATAC<br>ATTAATCCTAATACTGGTTTTACTGAATATAGTCAGAAATTCAAGGACAA<br>GGCCACATTGACTGCAGTCAAGTCCTCCAGCACAGCCTATATACAACTGA<br>CCAGCCTGACATCTGATGACTCTGCAGTCTATTACTGTGCAAGAGAGAAC<br>TATAGGTACGACGGGGCTATGGACTACTGGGGTCAAGGAACCCTCAGTCAC<br>CGTCTCCTCA (SEQ ID NO: 83) |
| light chain | GATATTGTGCTAACTCAGTCTCCAGCACTCATGGCTGCATTTCCAGGGGA<br>CAGGGTCACCATCACCTGCAGTGTCAGCTCAAGTGTAAGTTCCAGCAACT<br>TGCACTGGTACCAACAGAAGTCAGAAACCTCCCCCAAACCCTGGATTTAT<br>GGCACATCCACCCTGGCTTCTGGAGTCCCTGTTCGCTTCAGTGGCAGTGG<br>ATCTGGGACCTCTTATTCTCTCACAATCAGCAGCATGGAGGCTGAAGATG<br>CTGCCACTTATTACTGTCAACAGTGGAGTAGTTACCCACTCACGTTCGGT<br>GCTGGGACCAAGCTGGAGCTGAAACGG (SEQ ID NO: 84) |
| 43-1.3 heavy chain | GGTGAACTGCAGGAGTCAGGGCCTCAGGTGGTTAGGCCTGGGACTTCAGT<br>GAAGATATCCTGCAAGGCTTCTGGTTATTCATTTTCCAACTACTGGATGC<br>ACTGGGTGAAGCAGAGGCCTGGACAAGGTCTTGAGTGGATTGGCGTGATT<br>GATCCTTCCGATAGTGAAACTAGATTAAATCAGAAGTTCAAGGACAAGGC<br>CACATTGACTGTAGACAAATCCTCCAGTACAGCCTACATGCAACTCAGCA<br>GCCCGACATCTGAGGACTCTGCGATCTATTATTGTGCAAGATCACAGTTC<br>GGGCTACGTTTTGCTTACTGGGGCCAAGGGACTCTGGTCACTGTCTCTGC<br>A (SEQ ID NO: 85) |
| light chain | GACATTGTGATGACCCAGTCTCCATCCTCCATGACTGTGACAGCAGGAGA<br>GAAGGTCACTATGAGCTGCCAGTCCAGTCAGAGTCTATTCAACAGTGGAA<br>CTCAAAAGAACTACTTGACCTGGTACCAGCAGAAACCAGGACAGCCTCCT<br>AAACTGTTGATCTCCTGGGCATCCACTAGGGATTCTGGGGTCCCTGATCG<br>CTTCACAGGCAGTGGATCTGGAACAGATTTCACTCTCACCATTAACGGTG<br>TGCAGGCTGAAGACCTGGCAGTTTATTTCTGTCAGAATGATTATGATTCT<br>CCGTACACGTTCGGAGGGGGGACGAAGCTGGAAATAAAACGG (SEQ ID<br>NO: 86) |
| 22-1.5 heavy chain | GAGGTGCAACTGCAGCAGTCAGGACCTGAGCTGGTGAAACCTGGGGCC<br>TCAGTGAAGATATCCTGCAAGGCTTCTGGATACACATTCACTGACTACAA<br>CATACACTGGGTGAAACAGAGCCCTGGAAAGAGCCTTGAGTGGATTGGAT<br>ATATTTATCCTGACAATGGTGATACTGGCTACAACCAGATTTTCAAGAAC<br>AAGGCCACATTGACTGTAGACACTTCGTCCAGCGCAGCCTACATGGAACT<br>CCGCAGCCTGACATCTGAGGACTCTGCAGTCTATTACTGTGTAAGACGGG<br>TCCTTTTGGACTCCTGGGGTCAAGGAACCTCAGTCACCGTCTCCTCA<br>(SEQ ID NO: 87) |
| fight chain | GATATCCAGATGACACAGACTACATCTTCCCTGTCTGCCTCTCTGGGAGA<br>CAGAGTCACCATCAGTTGCAGTGCAAGTCAGGACATTAACAATTTTTTAA<br>ACTGGTATCAGCAGAAACCAGATGGAACTATTAAACTCCTGATCTATTAC<br>ACATCAAGTTTACAGTCAGGAGTCCCGTCAAGGTTCAGTGGCAGTGGGTC<br>TGGGACAGATTATTCTCTCACCATCAGCAACCTGGAACCTGAAGATATTG<br>CCACTTACTATTGTCAACAATATAGTAAACTTCCTCGGACGTTCGGTGGA<br>GGCACCAAGCTGGAAATCAAACGG (SEQ ID NO: 88) |
| 82-1.1 heavy chain | GAGGTGCAGCTGCAGCAGTCAGGGGGAGGCTTAGTGCAGCCTGGAGGGTC<br>CCTGAAACTCTCCTGTGCAGCCTCTGGATTCACTTTCAGTAACTATGACA<br>TGTCTTGGATTCGCCAGACTCCAGACAAGAGGCTGGAGATGGTCGCAGCC<br>ATTAATAGTAATGGTGGTAGCACCTATTATCCAGACAGTGTGAAGGGCCG<br>ATTCACCATCTCCAGAGACAAAGCCAAGAACACCCTATACCTGCAAATGA<br>GCAGTCTGAAGTCTGAGGACACAGCCATGTATTACTGTGCGAGCCCTAAT<br>GGTTACGGAGCTATGGACTACTGGGGTCAAGGAACCTCAGTCACCGTCTC<br>CTCA (SEQ ID NO: 89) |
| fight chain | GATATTGTGATAACCCAGACTCCACTCACTTTGTCGGTTACCATTGGACA<br>ACCAGCTTCCATCTCTTGCAAGTCACGTCAGAGCCTCTTAGATAGTGATG<br>GAAAAACCTATTTAAATTGGTTATTACAGAGGCCAGGCGAGTCTCCAAAG<br>CTCCTAATCTATCTGGTGTCTAAACTGGACTCTGGAGTCCCTGACAGGTT<br>CACTGGCAGTGGATCAGGGACAGATTTCACACTGAAAATCAGCAGAGTGG<br>AGGCTGAGGATTTGGGAGTTTATTACTGCTTGCAAGCTACACATTTTCCG<br>TGGACGTTCGGTGGAGGCACCAAGCTGGAAATCAAACGG (SEQ ID<br>NO: 90) |

2.2 Sandwich (Capture) ELISA

2.2.1 Serotype-Specific mAbs as Capture Antibodies

The four serotype-specific mAbs of the present invention were used as capture antibodies in sandwich (capture) ELISA. FIG. 1A shows the basic design of the sandwich (capture) ELISA using the serotype-specific mAbs of the present invention as capture antibodies, paired with cross-reactive mAbs as detection antibodies.

Figure 1B:
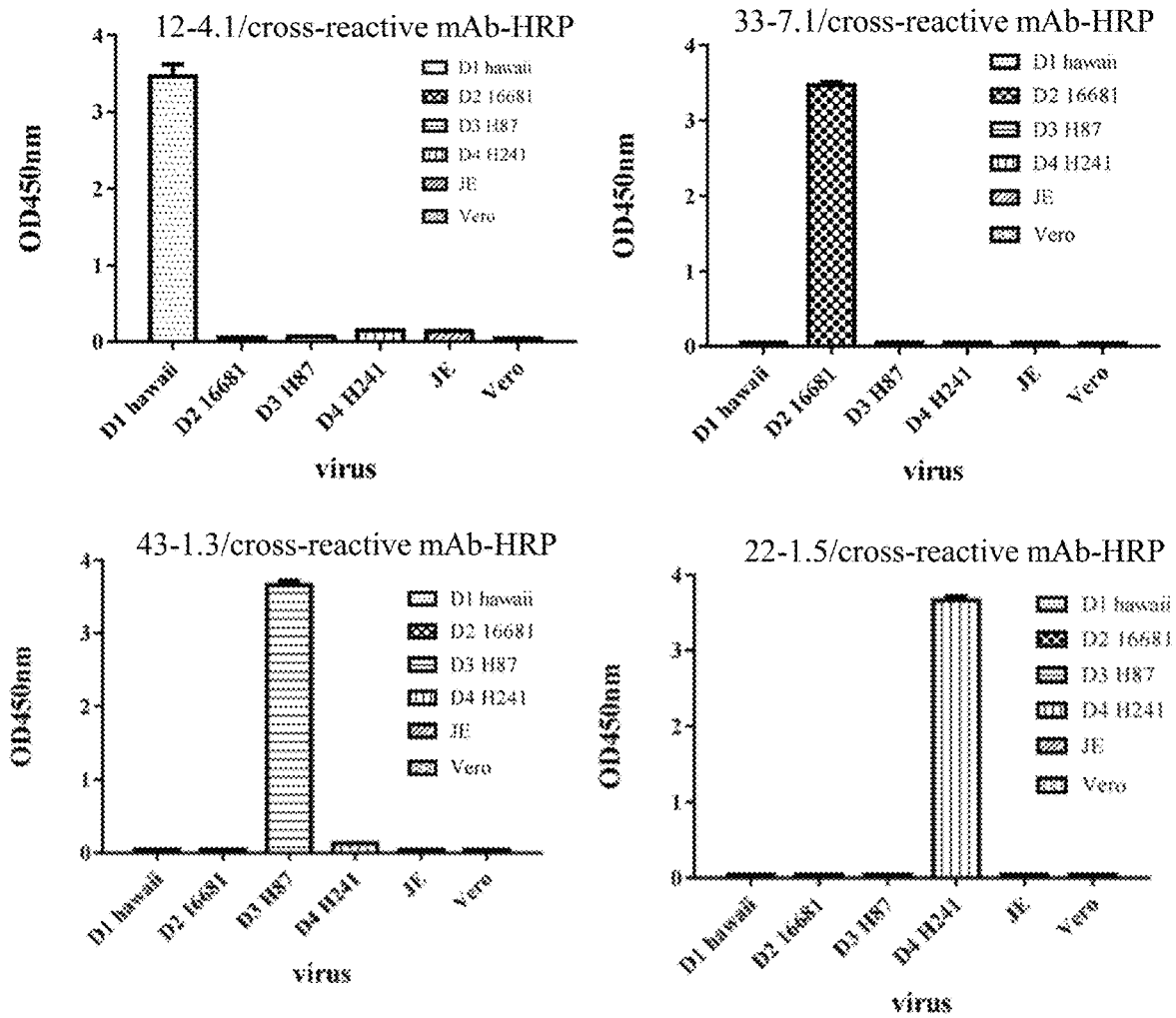
FIG. 1B shows the results of detection in the sandwich (capture) ELISA using the serotype-specific mAbs of the present invention, 12-4.1, 33-7.1, 43-1.3, and 22-1.5, as capture antibodies, paired with a serotype cross-reactive antibody to dengue virus, as detection antibodies. In this assay, cell culture supernatants from Vero cells infected with DENV1, DENV2, DENV3, DENV4, or JEV were used as sources of NS1 antigens, and supernatant from non-infected Vero cells was used a negative control.

Microwell plates were coated with serotype-specific mAbs of the present invention as capture antibodies and incubated overnight at 4° C. The wells were then blocked and washed. The cell culture supernatants of Vero cells infected with different serotype DENVs (DENV1 Hawaii, DENV2 16681, DENV3 H87 and DENV4 H241) or Japanese encephalitis (JE) virus or the cell culture supernatants of non-infected Vero cells (a negative control) were separately added to the wells and incubated at 37° C. for one hour. After washing, cross-reactive mAbs labelled with horseradish peroxidase (HRP), were added to the wells and incubated at 37° C. for one hour. The wells were washed again and 3,3',5,5'-tetramethylbenzidine (TMB), was added as a substrate of HRP to the wells. The absorbance was read at 450 nm. As shown in FIG. 1B, the serotype-specific mAbs of the present invention were demonstrated to successfully act as capture antibodies in sandwich (capture) ELISA, exhibiting superior serotype specificity without cross-reaction with other flavivirus (Japanese Encephalitis (JE) Virus).

2.2.2 Serotype-Specific mAbs as Detection Antibodies

Figure 2A:
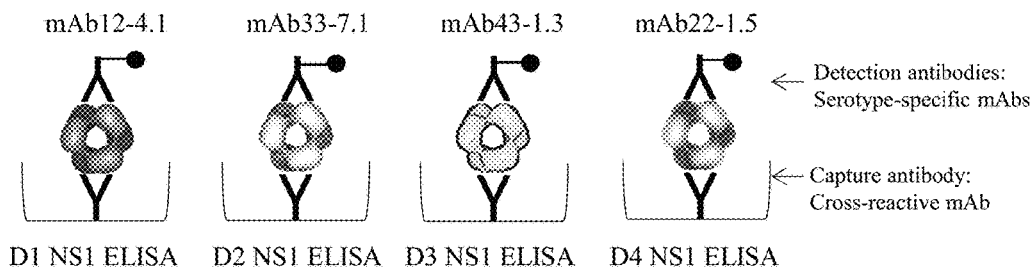
FIG. 2A shows the basic design of the sandwich (capture) ELISA using the serotype-specific mAbs of the present invention as detection antibodies, paired with a serotype cross-reactive antibody to dengue virus as capture antibodies.

The four serotype-specific mAbs of the present invention were used as detection antibodies in sandwich (capture) ELISA. FIG. 2A shows the basic design of the sandwich (capture) ELISA using the serotype-specific mAbs of the present invention as detection antibodies, paired with cross-reactive mAbs as capture antibodies.

Figure 2B:
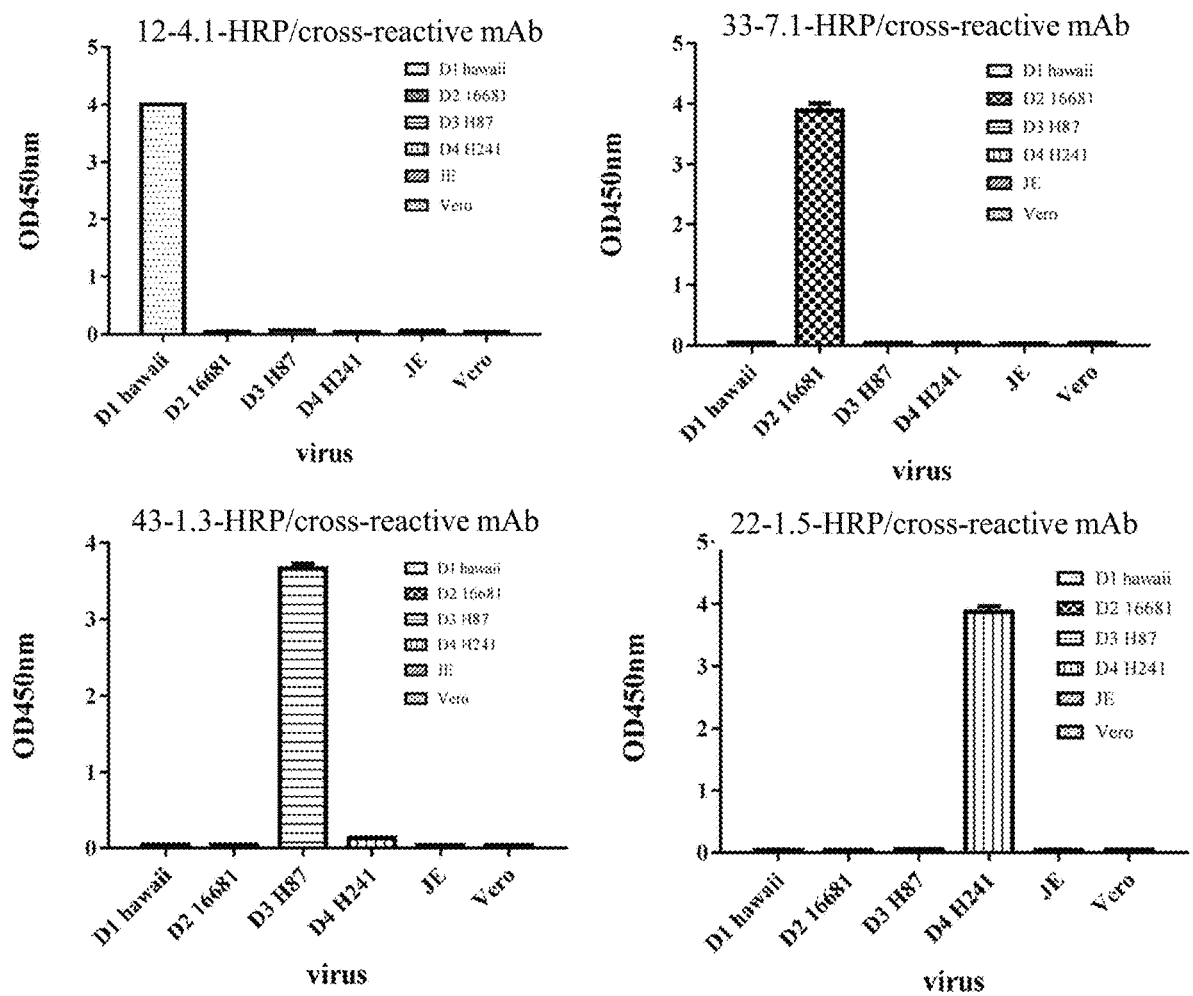
FIG. 2B shows the detection results of the sandwich (capture) ELISA using the serotype-specific mAbs of the present invention, 12-4.1, 33-7.1, 43-1.3, and 22-1.5, as detection antibodies, paired with a serotype cross-reactive antibody to dengue virus, as capture antibodies. In this assay, cell culture supernatants from Vero cells infected with DENV1, DENV2, DENV3, DENV4, or JEV were used as sources of NS1 antigens, and supernatant from non-infected Vero cells was used a negative control.

Microwell plates were coated with cross-reactive mAbs as capture antibodies and incubated overnight at 4° C. The wells were then blocked and washed. The cell culture supernatants of Vero cells infected with different serotype DENVs (DENV1 Hawaii, DENV2 16681, DENV3 H87 and DENV4 H241) or Japanese encephalitis (JE) virus or the cell culture supernatants of non-infected Vero cells (a negative control) were separately added to the wells and incubated at 37° C. for one hour. After washing, serotype-specific mAbs of the present invention labelled with horseradish peroxidase (HRP), were added to the wells and incubated at 37° C. for one hour. The wells were washed again and 3,3',5,5'-tetramethylbenzidine (TMB), was added as a substrate of HRP to the wells. The absorbance was read at 450 nm. As shown in FIG. 2B, the serotype-specific mAbs of the present invention were demonstrated to successfully act as detection antibodies in sandwich (capture) ELISA, exhibiting superior serotype specificity without cross-reaction with other flavivirus (Japanese encephalitis (JE) virus).

2.2.3 Detection Limits

Figure 3:
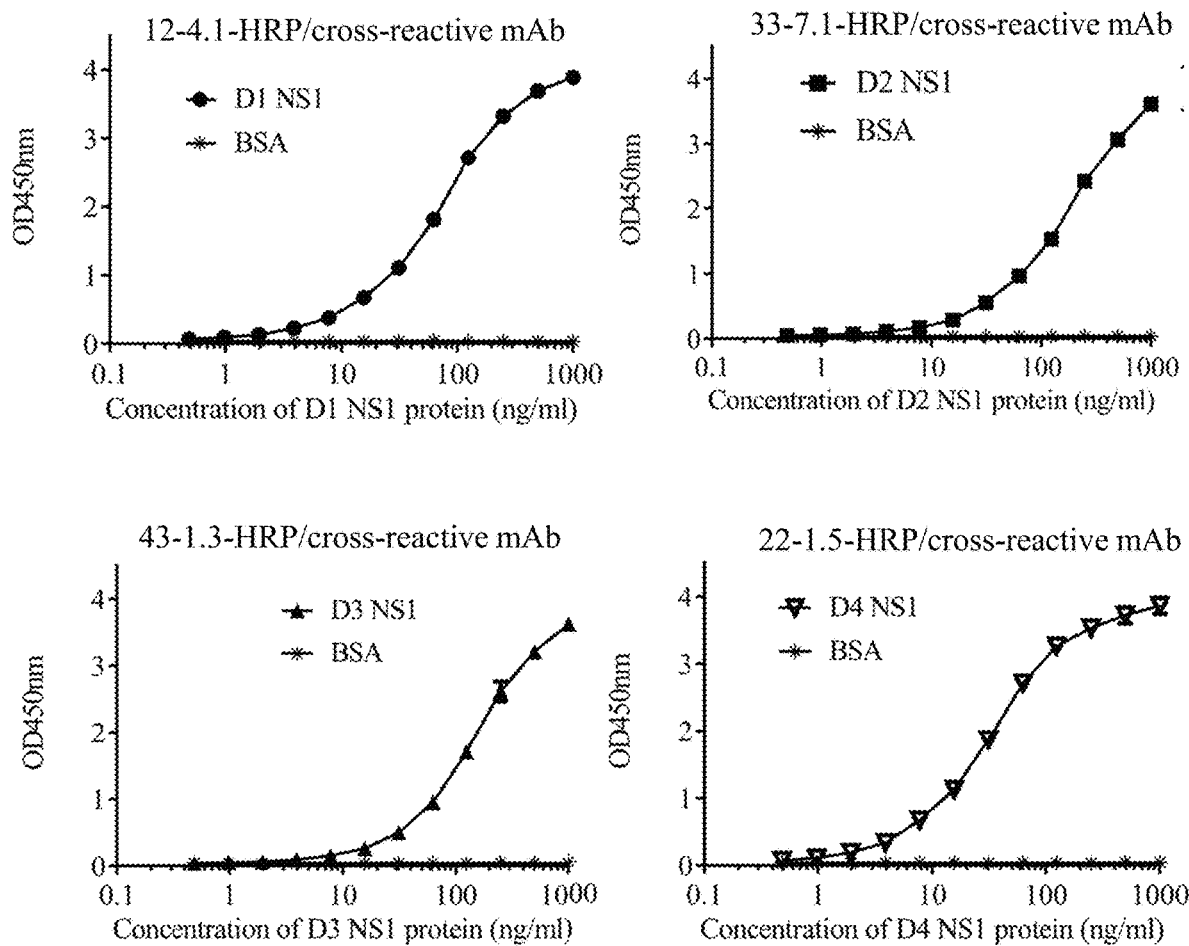
FIG. 3 shows the sensitivities of the sandwich (capture) ELISA using the serotype-specific mAbs of the present invention, 12-4.1, 33-7.1, 43-1.3, and 22-1.5, as detection antibodies, paired with a serotype cross-reactive antibody to dengue virus, as capture antibodies. Capture ELISA was performed with serial diluted and purified NS1 proteins of each DENV serotype to determine the detection limits of the serotype-specific mAbs of the present invention. Bovine serum albumin (BSA) was used to establish the baseline. Each data point represents the mean±SD of three replicate tests.

Capture ELISA was performed with serial diluted and purified NS1 proteins of each DENV serotype to determine the detection limits of the serotype-specific mAbs of the present invention. Table 4 and FIG. 3 shows the results.

TABLE 4

Detection limits of four serotype-specific NS1 capture ELISA of the present invention and commercially available Platelia Dengue NS1 AG ELISA

| NS1 detection assays | Minimum detectable concentration of NS1 proteins (ng/ml) | | | |
|---|---|---|---|---|
| | D1 | D2 | D3 | D4 |
| Four serotype-specific NS1 capture ELISA | 1.953 | 3.906 | 3.906 | 0.977 |
| Platelia Dengue NS1 AG ELISA | 3.906 | 31.250 | 0.977 | 7.813 |

Sensitivity comparison between the four serotype-specific NS1 capture ELISA and the commercially available Platelia Dengue NS1 AG ELISA in detecting NS1. Each NS1 protein serotype was immunoaffinity-purified and serially diluted prior to performing this analysis.

The results show that the capture ELISA using the serotype-specific mAbs of the present invention achieves superior sensitivity, ranging from 1 to 4 ng/ml of DENV1-4 NS1 proteins, comparable to the commercially available DENY ELISA kit (Pleterlia NS1 Ag ELISA, Bio-Rad) while the commercial kit cannot distinguish the serotypes.

2.3 Strip

Figure 4:
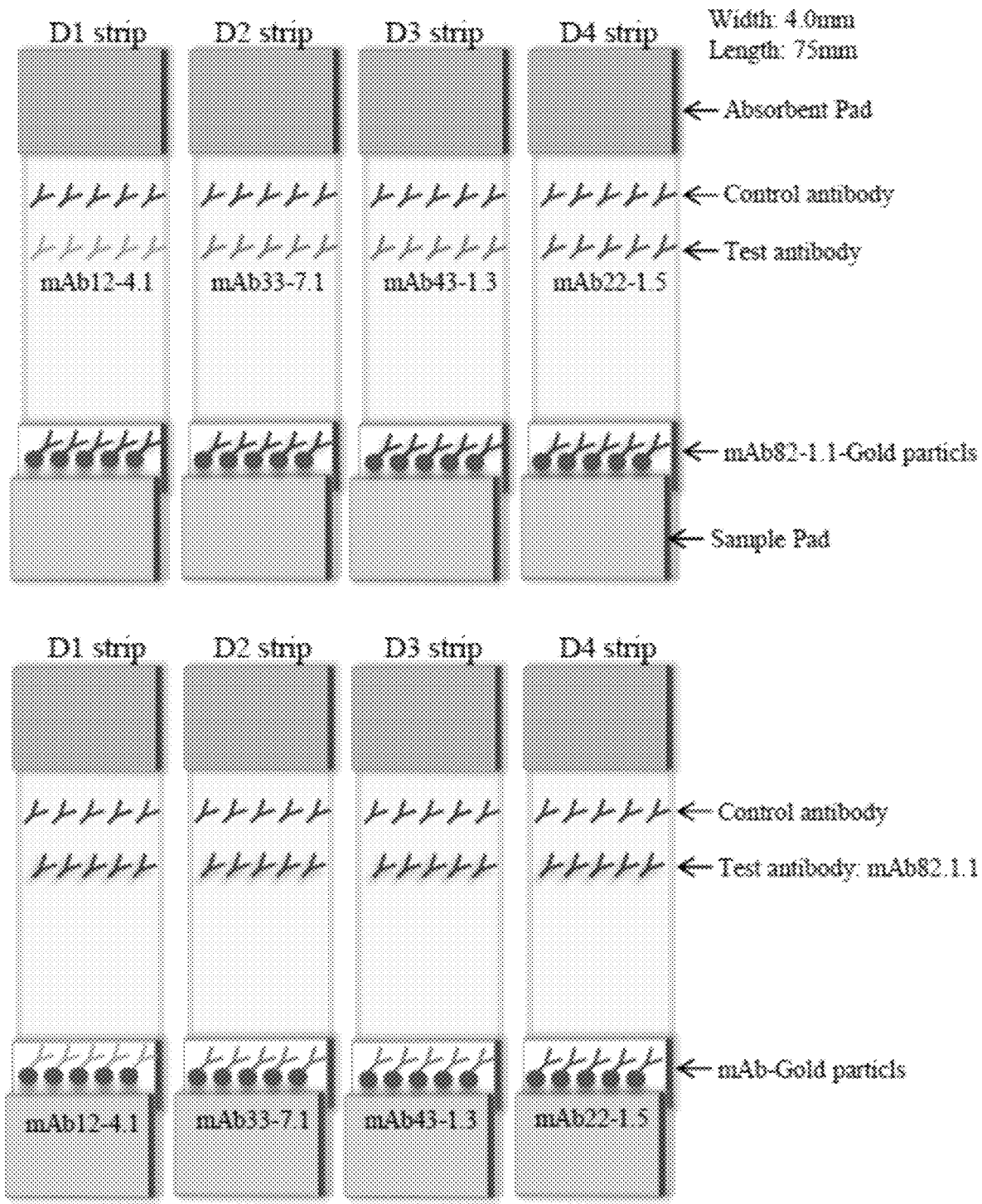
FIG. 4 shows the basic design of the sandwich strip using the serotype-specific mAbs of the present invention as capture antibodies (upper panel) or detection antibodies (lower panel), paired with a serotype cross-reactive antibody to dengue virus (mAb82-1.1).

The four serotype-specific mAbs of the present invention were also used to develop strips for DENV detection. FIG. 4 shows the basic design of serotyping NS1 strip using the serotype-specific mAbs of the present invention as capture antibodies (upper panel) or detection antibodies (detection panel), paired with cross reactive mAbs.

Figure 5:
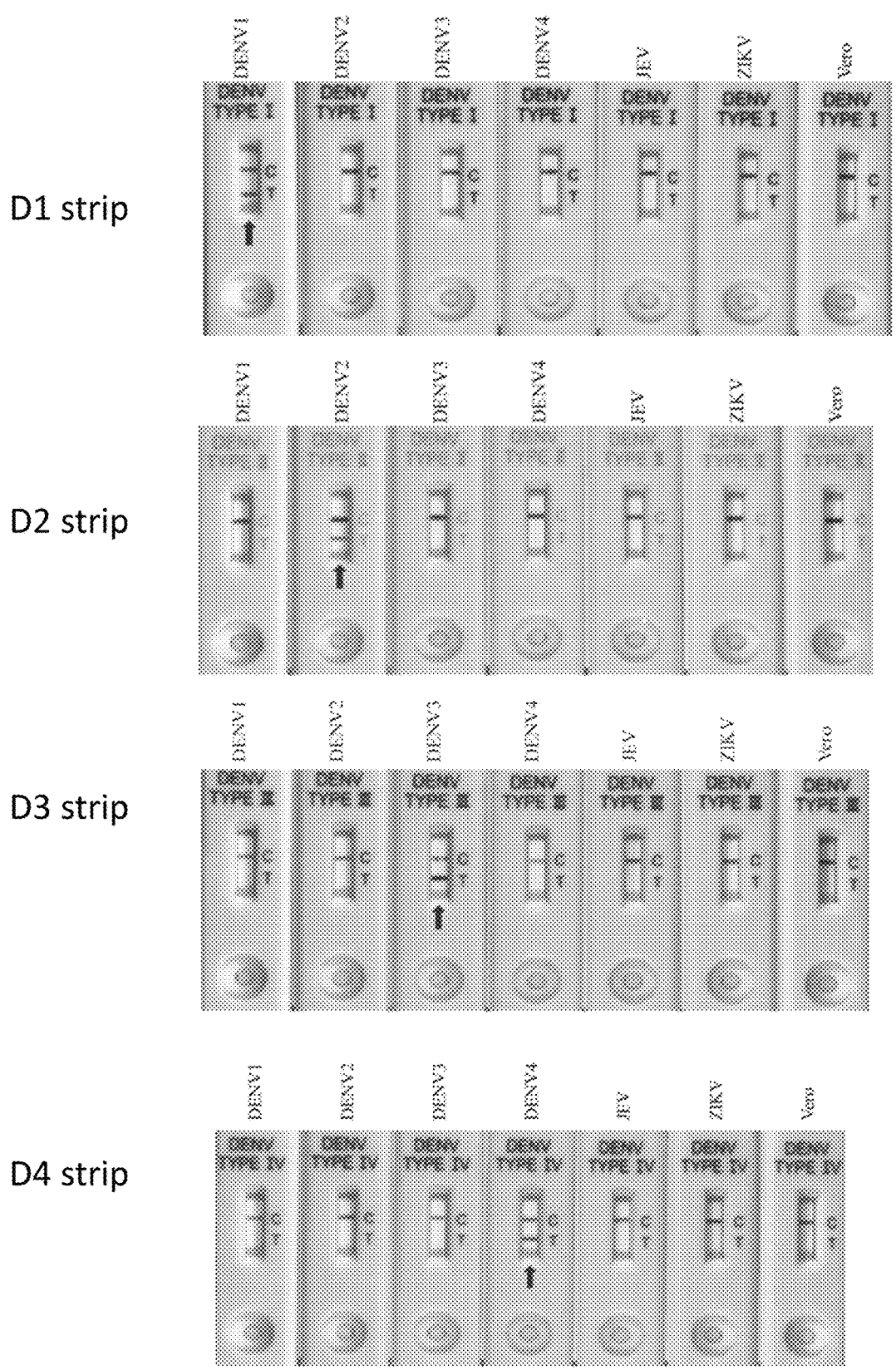
FIG. 5 shows the specificities of the sandwich strip of the present invention. Serotype-specific mAbs 12-4.1, 33-7.1, 43-1.3, and 22-1.5, paired with a serotype cross-reactive antibody to dengue virus (mAb82-1.1), were used as capture and detection antibodies and then tested for binding specificity. In this assay, cell culture supernatants from Vero cells infected with DENV1, DENV2, DENV3, DENV4, or JEV were used as sources of NS1 antigens, and supernatant from non-infected Vero cells was used a negative control.
Figure 6A:
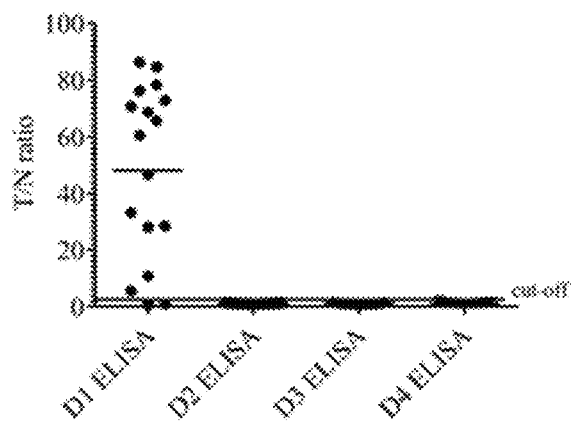
FIG. 6A to FIG. 6F include charts showing the specificities of the sandwich (capture) ELISA of the present invention for testing sera of acute febrile patients.
Figure 6B:
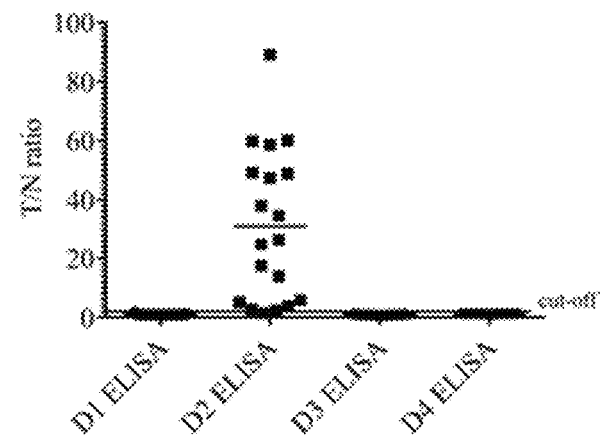
Figure 6C:
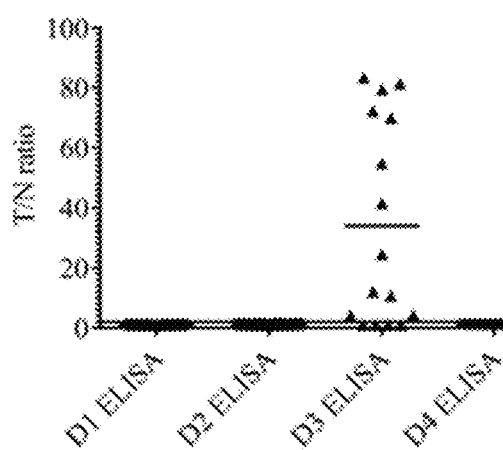
Figure 6D:
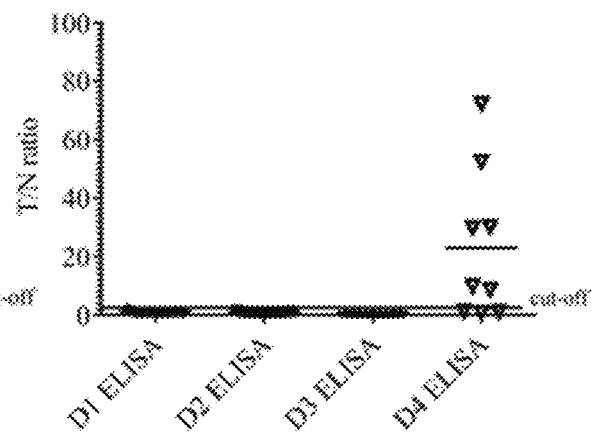
Figures 6E, 6F:
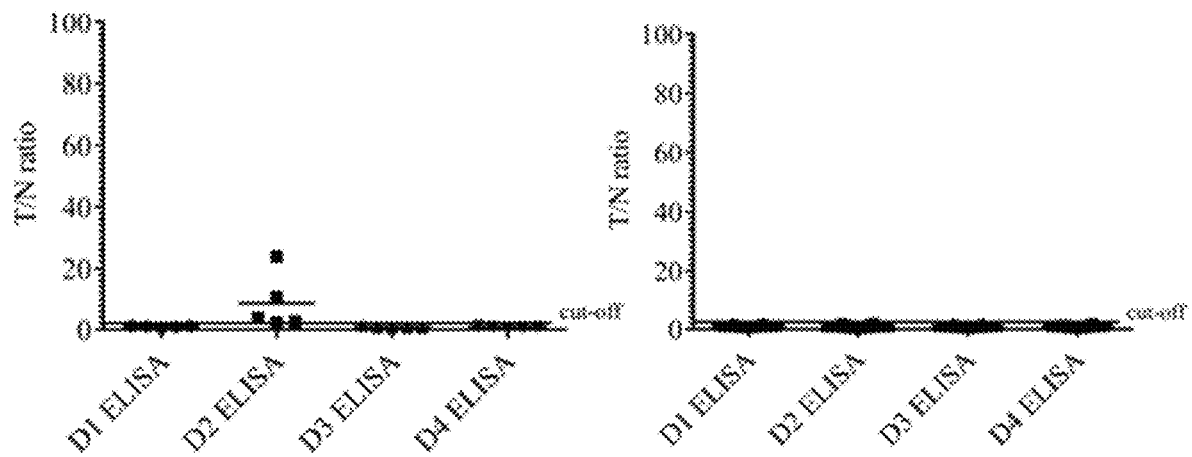

As shown in FIG. 5, the serotype-specific mAbs of the present invention (12-4.1, 33-7.1, 43-1.3, and 22-1.5) were demonstrated to successfully act as capture antibodies, paring with the cross-reactive mAb of the present invention (82.1.1) as detection antibodies, in serotyping NS1 strip, exhibiting superior serotype specificity to DENV1, DENV2, DENV3 and DENV4 (from top to bottom), respectively, without cross-reaction with other flavivirus (Japanese encephalitis (JE) virus and Zika virus (ZIKV)).

In addition, the detection limits of the serotype-specific mAbs of the present invention in strips were determined. Table 5 shows the results.

TABLE 5

Detection limits of four serotype-specific NS1 strips, Bio-Rad Dengue NS1 AG rapid test, and SD dengue NS1 Ag rapid test

| | Minimum detectable concentration of NS1 proteins (ng/ml) | | | |
|---|---|---|---|---|
| | D1 | D2 | D3 | D4 |
| four serotype-specific NS1 strips | 125 | 62.5 | 62.5 | 62.5 |
| Bio-Rad dengue NS1 Ag | 31.25 | 125~250 | 31.25 | 62.5 |
| SD dengue NS1 Ag | 62.5 | 125~250 | 31.25 | 125 |

Sensitivity of the four serotype NS1 strips in detecting NS1 protein. Each NS1 protein serotype was immunoaffinity-purified and serially diluted prior to performing this analysis.

The results show that the NS1 strips using the serotype-specific mAbs of the present invention achieves superior sensitivity, ranging from 62.5 to 125 ng/ml of DENV1-4 NS1 proteins, comparable to the commercially available DENY strip kits, while these commercial kits cannot distinguish the serotypes.

2.4 Clinical Tests

A total of 146 clinical serum samples were collected to determine the sensitivity and specificity of sandwich (capture) ELISA using the four serotype-specific mAbs of the present invention.

The 146 clinical serum samples were collected between one (1) and seven (7) days after the onset of illness and analyzed by conventional serotyping RT-PCR, dengue specific IgM/IgG capture ELISA, commercial dengue NS1 Ag ELISA methods, and serotype-specific NS1 capture ELISA of the present invention. Table 6 shows the results. FIG. 6 shows the specificities of the sandwich (capture) ELISA of the present invention for testing sera of acute febrile patients.

TABLE 8.1

| ELISA test | D1 | D2 | D3 | D4 |
|---|---|---|---|---|
| No. of all positive[a] | 17 | 19 | 16 | 9 |
| No. of true positive | 15 | 18 | 12 | 6 |
| No. of true negative | 80 | 80 | 80 | 80 |
| No. of false positive | 0 | 0 | 0 | 0 |
| No. of false negative | 2 | 1 | 4 | 3 |

TABLE 6

Examination of acute clinical sera by RT-PCR, IgM/IgG, Platelia Dengue NS1 AG ELISA, and four serotype-specific NS1 capture ELISA of the present invention

| Day that sera was collected (post onset of illness) | Total number of samples | RT-PCR serotyping[b] | | | | IgM/IgG[c] | Platelia NS1 Ag ELISA | Negative[d] | Four serotype-specific NS1 capture ELISA of the present invention | | | |
|---|---|---|---|---|---|---|---|---|---|---|---|---|
| | | D1 | D2 | D3 | D4 | | | | D1 | D2 | D3 | D4 |
| 1 | 45 | 6 | 4 | 4 | 4 | 0 | 14 | 27 | 5 | 4 | 4 | 3 |
| 2 | 46 | 4 | 7 | 8 | 1 | 2 | 19 | 24 | 3 | 9 | 6 | 0 |
| 3 | 21 | 3 | 1 | 1 | 2 | 0 | 4 | 14 | 3 | 1 | 0 | 2 |
| 4 | 12 | 2 | 3 | 2 | 1 | 0 | 8 | 4 | 2 | 3 | 1 | 1 |
| 5 | 7 | 0 | 2 | 0 | 0 | 1 | 2 | 4 | 0 | 2 | 0 | 0 |
| 6 | 6 | 1 | 1 | 1 | 0 | 1 | 4 | 2 | 1 | 2 | 1 | 0 |
| 7 | 1 | 0 | 0 | 0 | 0 | 0 | 0 | 1 | 0 | 0 | 0 | 0 |
| Unknown[a] | 8 | 1 | 1 | 0 | 1 | 1 | 4 | 4 | 1 | 2 | 0 | 0 |
| total | 146 | 17 | 19 | 16 | 9 | 5 | 55 | 80 | 15 | 23 | 12 | 6 |

[a] No information pertaining to sera collection date was available.
[b] Serotype-specific one-step SYBR Green I-based RT-PCR
[c] Negative result by RT-PCR but positive result both by dengue virus specific IgM/IgG capture ELISA and Platelia Dengue NS1 AG ELISA
[d] Negative result by RT-PCR, dengue virus specific IgM/IgG capture ELISA, and Platelia Dengue NS1 AG ELISA The results show that the 146 clinical serum samples were confirmed to include seventeen (17) samples of DENV1 serotype, nineteen (19) samples of DENV2 serotype, sixteen (16) samples of DENV3 serotype, and nine (9) samples of DENV4 serotype; five (5) samples were determined negative by RT-PCR but positive by dengue virus specific IgM/IgG capture ELISA; fifty-five (55) samples were determined positive by Platelia NS1 Ag ELISA; and eighty (80) samples were determined negative by all the tested methods.

The results show that sandwich (capture) ELISA using the four serotype-specific mAbs of the present invention exhibit excellent sensitivity and specificity, wherein D1 ELISA (mAb12-4.1) capable of detecting 15 DENV1 samples from 17 DENV1 samples, D2 ELISA (mAb33-7.) capable of detecting 18 DENV2 samples from 19 DENV2 samples, D3 ELISA (mAb43-1.3) capable of detecting 12 DENV3 samples from 16 DENV3 samples, and D4 ELISA (mAb22-1.5) capable of detecting 6 DENV4 samples from 9 DENV1 samples; the five (5) samples that were not detected by serotype RT-PCR were determined positive and identified as DENV2; and all the eighty (80) negative samples were determined as negative as well without false positive results. FIG. 6A to FIG. 6F show the specificities of the sandwich (capture) ELISA of the present invention for testing sera of acute febrile patients.

Tables 8.1 and 8.2 summarize the results of sensitivity and specificity of sandwich (capture) ELISA using the four serotype-specific mAbs of the present invention.

TABLE 8.1-continued

| ELISA test | D1 | D2 | D3 | D4 |
|---|---|---|---|---|
| Serotype specificity | 100 | 100 | 100 | 100 |
| Serotype sensitivity | 0.882 | 0.947 | 0.75 | 0.666 |

[a] Serotype by serotype-specific one-step SYBR Green 1-based RT-PCR

TABLE 8.2

| No. of sera with NS1 result of positive | True status: Disease (66); No disease (80) | | | | |
|---|---|---|---|---|---|
| | % sensitivity (95% CI) | % specificity (95% CI) | % accuracy (95% CI) | % PPV (95% CI) | % NPV (95% CI) |
| 56 | 84.85 (73.9-92.49) | 100 (95.49-100) | 93.15 (87.76-96.67) | 100 (93.63-100) | 88.89 (80.51-94.54) |

PPV = positive predictive value;
NPV = negative predictive value

The results show the sandwich (capture) ELISA based on the four serotype-specific mAbs of the present invention is capable to detect and distinguish the four dengue virus serotypes in serum samples even after the early five (5) days post onset of illness, exhibiting overall 100% specificity and 84.8% sensitivity.

What is claimed is:

1. An isolated antibody or antigen-binding fragment thereof specific for dengue virus, wherein the isolated antibody is selected from the group consisting of:
   (i) a first antibody specific for dengue virus serotype 1 (DENV1) comprising
      (a) a heavy chain variable region ($V_H$) which comprises a heavy chain complementary determining region (HC CDR1) of SEQ ID NO: 2, a heavy chain complementary determining region 2 (HC CDR2) of SEQ ID NO: 4, and a heavy chain complementary determining region 3 (HC CDR3) of SEQ ID NO: 6; and
      (b) a light chain variable region ($V_L$) which comprises a light chain complementary determining region 1 (LC CDR1) of SEQ ID NO: 9, a light chain complementary determining region (LC CDR2) of SEQ ID NO: 11, and a light chain complementary determining region 3 (LC CDR3) of SEQ ID NO: 13;
   (ii) a second antibody specific for dengue virus serotype 2 (DENV2) comprising
      (a) a $V_H$ which comprises a HC CDR1 of SEQ ID NO: 16, a HC CDR2 of SEQ ID NO: 18, and a HC CDR3 of SEQ ID NO: 20; and
      (b) a $V_L$ which comprises a LC CDR1 of SEQ ID NO: 23, a LC CDR2 of SEQ ID NO: 25, and a LC CDR3 of SEQ ID NO: 27;
   (iii) a third antibody specific for dengue virus serotype 3 (DENV3) comprising
      (a) a $V_H$ which comprises a HC CDR1 of SEQ ID NO: 30, a HC CDR2 of SEQ ID NO: 32, and a HC CDR3 of SEQ ID NO: 34; and
      (b) a $V_L$ which comprises a LC CDR1 of SEQ ID NO: 37, a LC CDR2 of SEQ ID NO: 39, and a LC CDR3 of SEQ ID NO: 41;
   (iv) a fourth antibody specific for dengue virus serotype 4 (DENV4) comprising
      (a) a $V_H$ which comprises a HC CDR1 of SEQ ID NO: 44, a HC CDR2 of SEQ ID NO: 46, and a HC CDR3 of SEQ ID NO: 48; and
      (b) a $V_L$ which comprises a LC CDR1 of SEQ ID NO: 51, a LC CDR2 of SEQ ID NO: 53, and a LC CDR3 of SEQ ID NO: 55; and
   (v) a fifth antibody cross-reactive to DENV1, DENV2, DENV3 and DENV4 comprising
      (a) a $V_H$ which comprises a HC CDR1 of SEQ ID NO: 58, a HC CDR2 of SEQ ID NO: 60, and a HC CDR3 of SEQ ID NO: 62; and
      (b) a $V_L$ which comprises a LC CDR1 of SEQ ID NO: 65, a LC CDR2 of SEQ ID NO: 67, and a LC CDR3 of SEQ ID NO: 69; and
   (vi) any combination of (i) to (v).

2. The isolated antibody or antigen-binding fragment of claim 1, wherein
   (i) the first antibody comprises a $V_H$ that comprises SEQ ID NO: 71 and a $V_L$ comprising SEQ ID NO: 72;
   (ii) the second antibody comprises a $V_H$ comprising SEQ ID NO: 73 and a $V_L$ comprising SEQ ID NO: 74;
   (iii) the third antibody comprises a $V_H$ comprising SEQ ID NO: 75 and a $V_L$ comprising SEQ ID NO: 76;
   (iv) the fourth antibody comprises a $V_H$ comprising SEQ ID NO: 77 and a $V_L$ comprising SEQ ID NO: 78; and/or
   (v) the fifth antibody comprises a $V_H$ comprising SEQ ID NO: 79 and a $V_L$ comprising SEQ ID NO: 80.

3. The isolated antibody or antigen-binding fragment of claim 1, wherein the antigen-binding fragment is selected from the group consisting of scFv, (scFv)2, Fab, Fab', and F(ab')2 of the isolated antibody specific for dengue virus.

4. A composition comprising the isolated antibody or antigen-binding fragment thereof of claim 1.

5. The composition of claim 4, which is a pharmaceutical or diagnostic composition for use in treatment or diagnosis of dengue virus disease.

6. The composition of claim 4, which comprises a pharmaceutically acceptable carrier.

7. A method for detecting dengue virus in a sample suspected of containing said dengue virus, comprising contacting the sample with an isolated antibody or antigen-binding fragment thereof specific for dengue virus, and assaying binding of the antibody with said sample, wherein the isolated antibody is selected from the group consisting of:
  (i) a first antibody specific for dengue virus serotype 1 (DENV1) that comprises a $V_H$ comprising a HC CDR1 of SEQ ID NO: 2, a HC CDR2 of SEQ ID NO: 4, and a HC CDR3 of SEQ ID NO: 6; and a $V_L$ comprising a LC CDR1 of SEQ ID NO: 9, a LC CDR2 of SEQ ID NO: 11, and a LC CDR3 of SEQ ID NO: 13;
  (ii) a second antibody specific for dengue virus serotype 2 (DENV2) that comprises a $V_H$ comprising a HC CDR1 of SEQ ID NO: 16, a HC CDR2 of SEQ ID NO: 18, and a HC CDR3 of SEQ ID NO: 20; and a $V_L$ comprising a LC CDR1 of SEQ ID NO: 23, a LC CDR2 of SEQ ID NO: 25, and a LC CDR3 of SEQ ID NO: 27;
  (iii) a third antibody specific for dengue virus serotype 3 (DENV3) that comprises a $V_H$ comprising a HC CDR1 of SEQ ID NO: 30, a HC CDR2 of SEQ ID NO: 32, and a HC CDR3 of SEQ ID NO: 34; and a $V_L$ comprising a LC CDR1 of SEQ ID NO: 37, a LC CDR2 of SEQ ID NO: 39, and a LC CDR3 of SEQ ID NO: 41;
  (iv) a forth antibody specific for dengue virus serotype 4 (DENV4) that comprises a $V_H$ comprising a HC CDR1 of SEQ ID NO: 44, a HC CDR2 of SEQ ID NO: 46, and a HC CDR3 of SEQ ID NO: 48; and a $V_L$ comprising a LC CDR1 of SEQ ID NO: 51, a LC CDR2 of SEQ ID NO: 53, and a LC CDR3 of SEQ ID NO: 55; and
  (v) any combination of (i) to (iv).

8. The method of claim 7, wherein each of the first antibody, the second antibody, the third antibody and the fourth antibody, is paired with a partner antibody.

9. The method of claim 8, wherein the partner antibody is a serotype cross-reactive antibody to dengue virus which comprises
  (a) a $V_H$ which comprises a HC CDR1 of SEQ ID NO: 58, a HC CDR2 of SEQ ID NO: 60, and a HC CDR3 of SEQ ID NO: 62; and
  (b) a $V_L$ which comprises a LC CDR1 of SEQ ID NO: 65, a LC CDR2 of SEQ ID NO: 67, and a LC CDR3 of SEQ ID NO: 69.

10. The method of claim 7, wherein
  (i) binding of the first antibody with the sample is an indicative of the presence of DENV1 in the sample;
  (ii) binding of the second antibody to the dengue virus is an indicative of the presence of DENV2 in the sample;
  (iii) binding of the third antibody to the dengue virus is an indicative of the presence of DENV3 in the sample; and/or
  (iv) binding of the fourth antibody to the dengue virus is an indicative of the presence of DENV4 in the sample.

11. A kit for detecting the presence of dengue virus in a sample, wherein the kit comprises one or more antibodies specific to dengue virus, selected from the group consisting of:
  (i) a first antibody specific for dengue virus serotype 1 (DENV1) that comprises a $V_H$ comprising a HC CDR1 of SEQ ID NO: 2, a HC CDR2 of SEQ ID NO: 4, and a HC CDR3 of SEQ ID NO: 6; and a $V_L$ comprising a LC CDR1 of SEQ ID NO: 9, a LC CDR2 of SEQ ID NO: 11, and a LC CDR3 of SEQ ID NO: 13;
  (ii) a second antibody specific for dengue virus serotype 2 (DENV2) that comprises a $V_H$ comprising a HC CDR1 of SEQ ID NO: 16, a HC CDR2 of SEQ ID NO: 18, and a HC CDR3 of SEQ ID NO: 20; and a $V_L$ comprising a LC CDR1 of SEQ ID NO: 23, a LC CDR2 of SEQ ID NO: 25, and a LC CDR3 of SEQ ID NO: 27;
  (iii) a third antibody specific for dengue virus serotype 3 (DENV3) that comprises a $V_H$ comprising a HC CDR1 of SEQ ID NO: 30, a HC CDR2 of SEQ ID NO: 32, and a HC CDR3 of SEQ ID NO: 34; and a $V_L$ comprising a LC CDR1 of SEQ ID NO: 37, a LC CDR2 of SEQ ID NO: 39, and a LC CDR3 of SEQ ID NO: 41;
  (iv) a forth antibody specific for dengue virus serotype 4 (DENV4) that comprises a $V_H$ comprising a HC CDR1 of SEQ ID NO: 44, a HC CDR2 of SEQ ID NO: 46, and a HC CDR3 of SEQ ID NO: 48; and a $V_L$ comprising a LC CDR1 of SEQ ID NO: 51, a LC CDR2 of SEQ ID NO: 53, and a LC CDR3 of SEQ ID NO: 55;
  (v) any combination of (i) to (iv); and
  (vi) an optional partner antibody.

12. The kit of claim 11, wherein the partner antibody is a serotype cross-reactive antibody to dengue virus which comprises
  (a) a $V_H$ which comprises a HC CDR1 of SEQ ID NO: 58, a HC CDR2 of SEQ ID NO: 60, and a HC CDR3 of SEQ ID NO: 62; and
  (b) a $V_L$ which comprises a LC CDR1 of SEQ ID NO: 65, a LC CDR2 of SEQ ID NO: 67, and a LC CDR3 of SEQ ID NO: 69.

13. The kit of claim 11, wherein at least one of the serotype-specific antibodies or the partner antibody comprises a detectable label.

14. The kit of claim 13, wherein the detectable label is selected from the group consisting of an enzymatic label, a fluorescent label, a metal label and a radio label.

15. The kit of claim 13, wherein the detectable label is selected from the group consisting of gold nanoparticles, colored latex beads, magnetic particles, carbon nanoparticles, selenium nanoparticles.

16. The kit of claim 11, wherein the kit is an immunoassay kit.

17. The kit of claim 16, wherein the immunoassay is selected from the group consisting of ELISA (enzyme-linked immunosorbent assay), RIA (radioimmunoassay), FIA (fluorescence immunoassay), LIA (luminescence immunoassay), or ILMA immunoluminometric assay.

18. The kit of claim 16, wherein the immunoassay is in a lateral flow assay format.

19. The kit of claim 16, wherein the immunoassay is a sandwich assay.

20. A nucleic acid comprising a nucleotide sequence encoding a heavy chain variable region ($V_H$), a light chain variable region ($V_L$) or both, wherein the $V_H$ and $V_L$ are as set forth in claim 1.

21. An isolated host cell comprising the nucleic acid of claim 20.

* * * * *

SEQUENCE LISTING

<160> NUMBER OF SEQ ID NOS: 90

<210> SEQ ID NO 1
<211> LENGTH: 25
<212> TYPE: PRT
<213> ORGANISM: Artificial Sequence
<220> FEATURE:
<223> OTHER INFORMATION: 1Ab VH FW1

<400> SEQUENCE: 1

Glu Val Lys Leu Gln Glu Ser Gly Ala Glu Leu Ala Lys Pro Gly Ala
1               5                   10                  15

Ser Val Lys Met Ser Cys Arg Ala Ser
            20                  25

<210> SEQ ID NO 2
<211> LENGTH: 10
<212> TYPE: PRT
<213> ORGANISM: Artificial Sequence
<220> FEATURE:
<223> OTHER INFORMATION: 1Ab VH CDR1

<400> SEQUENCE: 2

Gly Tyr Thr Phe Thr Ser Tyr Trp Ile His
1               5                   10

<210> SEQ ID NO 3
<211> LENGTH: 14
<212> TYPE: PRT
<213> ORGANISM: Artificial Sequence
<220> FEATURE:
<223> OTHER INFORMATION: 1Ab VH FW2

<400> SEQUENCE: 3

Trp Val Lys Glu Arg Pro Gly Gln Gly Leu Glu Trp Ile Gly
1               5                   10

<210> SEQ ID NO 4
<211> LENGTH: 17
<212> TYPE: PRT
<213> ORGANISM: Artificial Sequence
<220> FEATURE:
<223> OTHER INFORMATION: 1Ab VH CDR2

<400> SEQUENCE: 4

Tyr Ile Thr Pro Asn Thr Gly Tyr Asn Glu Asn Ser Gln Lys Phe Arg
1               5                   10                  15

Gly

<210> SEQ ID NO 5
<211> LENGTH: 32
<212> TYPE: PRT
<213> ORGANISM: Artificial Sequence
<220> FEATURE:
<223> OTHER INFORMATION: 1Ab VH FW3

<400> SEQUENCE: 5

Lys Ala Thr Leu Thr Ala Asp Lys Ser Ser Asn Thr Ala Tyr Met Gln
1               5                   10                  15

Leu Ser Ser Leu Thr Ser Glu Asp Ser Ala Val Tyr Phe Cys Val Arg
            20                  25                  30

<210> SEQ ID NO 6
<211> LENGTH: 9
<212> TYPE: PRT

```
<213> ORGANISM: Artificial Sequence
<220> FEATURE:
<223> OTHER INFORMATION: 1Ab VH CDR3

<400> SEQUENCE: 6

Arg Thr Tyr Glu Gly Tyr Leu Asp Val
1               5

<210> SEQ ID NO 7
<211> LENGTH: 11
<212> TYPE: PRT
<213> ORGANISM: Artificial Sequence
<220> FEATURE:
<223> OTHER INFORMATION: 1Ab VH FW4

<400> SEQUENCE: 7

Trp Gly Ala Gly Thr Thr Val Thr Val Ser Ser
1               5                   10

<210> SEQ ID NO 8
<211> LENGTH: 23
<212> TYPE: PRT
<213> ORGANISM: Artificial Sequence
<220> FEATURE:
<223> OTHER INFORMATION: 1Ab VL FW1

<400> SEQUENCE: 8

Asp Ile Val Met Thr Gln Thr Pro Leu Ser Leu Pro Val Ser Leu Gly
1               5                   10                  15

Asp Gln Ala Ser Ile Ser Cys
            20

<210> SEQ ID NO 9
<211> LENGTH: 16
<212> TYPE: PRT
<213> ORGANISM: Artificial Sequence
<220> FEATURE:
<223> OTHER INFORMATION: 1Ab VL CDR1

<400> SEQUENCE: 9

Arg Ser Ser Gln Asn Leu Val His Asn Asn Gly Asn Thr Tyr Leu Glu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: 1Ab VL CDR2

<400> SEQUENCE: 10

Trp Tyr Leu Gln Lys Pro Gly Gln Ser Pro Lys Leu Leu Ile Tyr
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: 1Ab VL CDR2

<400> SEQUENCE: 11

Lys Val Ser Asn Arg Leu Ser
1               5

<210> SEQ ID NO 12
```

<211> LENGTH: 32
<212> TYPE: PRT
<213> ORGANISM: Artificial Sequence
<220> FEATURE:
<223> OTHER INFORMATION: 1Ab VL FW3

<400> SEQUENCE: 12

Gly Val Pro Asp Arg Phe Ser Gly Ser Gly Ser Gly Thr Asp Phe Thr
1               5                   10                  15
Leu Asn Ile Ser Arg Val Glu Ala Glu Asp Leu Gly Ile Tyr Tyr Cys
            20                  25                  30

<210> SEQ ID NO 13
<211> LENGTH: 9
<212> TYPE: PRT
<213> ORGANISM: Artificial Sequence
<220> FEATURE:
<223> OTHER INFORMATION: 1Ab VL CDR3

<400> SEQUENCE: 13

Phe Gln Ala Ser His Val Pro Arg Thr
1               5

<210> SEQ ID NO 14
<211> LENGTH: 11
<212> TYPE: PRT
<213> ORGANISM: Artificial Sequence
<220> FEATURE:
<223> OTHER INFORMATION: 1Ab VL FW4

<400> SEQUENCE: 14

Phe Gly Gly Gly Thr Lys Leu Glu Ile Lys Arg
1               5                   10

<210> SEQ ID NO 15
<211> LENGTH: 25
<212> TYPE: PRT
<213> ORGANISM: Artificial Sequence
<220> FEATURE:
<223> OTHER INFORMATION: 2Ab VH FW1

<400> SEQUENCE: 15

Glu Val Gln Leu Gln Glu Ser Gly Ala Glu Leu Ala Lys Pro Gly Ala
1               5                   10                  15
Ser Val Lys Met Ser Cys Lys Ala Ser
            20                  25

<210> SEQ ID NO 16
<211> LENGTH: 10
<212> TYPE: PRT
<213> ORGANISM: Artificial Sequence
<220> FEATURE:
<223> OTHER INFORMATION: 2Ab VH CDR1

<400> SEQUENCE: 16

Gly Tyr Thr Phe Thr Ser Tyr Trp Met His
1               5                   10

<210> SEQ ID NO 17
<211> LENGTH: 14
<212> TYPE: PRT
<213> ORGANISM: Artificial Sequence
<220> FEATURE:
<223> OTHER INFORMATION: 2Ab VH FW2

<400> SEQUENCE: 17

```
Trp Val Lys Gln Arg Pro Gly Gln Val Leu Glu Trp Ile Gly
1               5                   10
```

<210> SEQ ID NO 18
<211> LENGTH: 17
<212> TYPE: PRT
<213> ORGANISM: Artificial Sequence
<220> FEATURE:
<223> OTHER INFORMATION: 2Ab VH CDR2

<400> SEQUENCE: 18

```
Tyr Ile Asn Pro Asn Thr Gly Phe Thr Glu Tyr Ser Gln Lys Phe Lys
1               5                   10                  15

Asp
```

<210> SEQ ID NO 19
<211> LENGTH: 32
<212> TYPE: PRT
<213> ORGANISM: Artificial Sequence
<220> FEATURE:
<223> OTHER INFORMATION: 2Ab VH FW3

<400> SEQUENCE: 19

```
Lys Ala Thr Leu Thr Ala Val Lys Ser Ser Thr Ala Tyr Ile Gln
1               5                   10                  15

Leu Thr Ser Leu Thr Ser Asp Asp Ser Ala Val Tyr Tyr Cys Ala Arg
            20                  25                  30
```

<210> SEQ ID NO 20
<211> LENGTH: 11
<212> TYPE: PRT
<213> ORGANISM: Artificial Sequence
<220> FEATURE:
<223> OTHER INFORMATION: 2Ab VH CDR3

<400> SEQUENCE: 20

```
Glu Asn Tyr Arg Tyr Asp Gly Ala Met Asp Tyr
1               5                   10
```

<210> SEQ ID NO 21
<211> LENGTH: 11
<212> TYPE: PRT
<213> ORGANISM: Artificial Sequence
<220> FEATURE:
<223> OTHER INFORMATION: 2Ab VH FW4

<400> SEQUENCE: 21

```
Trp Gly Gln Gly Thr Ser Val Thr Val Ser Ser
1               5                   10
```

<210> SEQ ID NO 22
<211> LENGTH: 23
<212> TYPE: PRT
<213> ORGANISM: Artificial Sequence
<220> FEATURE:
<223> OTHER INFORMATION: 2Ab VL FW1

<400> SEQUENCE: 22

```
Asp Ile Val Leu Thr Gln Ser Pro Ala Leu Met Ala Ala Phe Pro Gly
1               5                   10                  15

Asp Arg Val Thr Ile Thr Cys
                20
```

<210> SEQ ID NO 23
<211> LENGTH: 12

```
<212> TYPE: PRT
<213> ORGANISM: Artificial Sequence
<220> FEATURE:
<223> OTHER INFORMATION: 2Ab VL CDR1

<400> SEQUENCE: 23

Ser Val Ser Ser Ser Val Ser Ser Ser Asn Leu His
1               5                   10

<210> SEQ ID NO 24
<211> LENGTH: 15
<212> TYPE: PRT
<213> ORGANISM: Artificial Sequence
<220> FEATURE:
<223> OTHER INFORMATION: 2Ab VL FW2

<400> SEQUENCE: 24

Trp Tyr Gln Gln Lys Ser Glu Thr Ser Pro Lys Pro Trp Ile Tyr
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: 2Ab VL CDR2

<400> SEQUENCE: 25

Gly Thr Ser Thr Leu Ala Ser
1               5

<210> SEQ ID NO 26
<211> LENGTH: 32
<212> TYPE: PRT
<213> ORGANISM: Artificial Sequence
<220> FEATURE:
<223> OTHER INFORMATION: 2Ab VL FW3

<400> SEQUENCE: 26

Gly Val Pro Val Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 27
<211> LENGTH: 9
<212> TYPE: PRT
<213> ORGANISM: Artificial Sequence
<220> FEATURE:
<223> OTHER INFORMATION: 2Ab VL CDR3

<400> SEQUENCE: 27

Gln Gln Trp Ser Ser Tyr Pro Leu Thr
1               5

<210> SEQ ID NO 28
<211> LENGTH: 11
<212> TYPE: PRT
<213> ORGANISM: Artificial Sequence
<220> FEATURE:
<223> OTHER INFORMATION: 2Ab VL FW4

<400> SEQUENCE: 28

Phe Gly Ala Gly Thr Lys Leu Glu Leu Lys Arg
1               5                   10
```

<210> SEQ ID NO 29
<211> LENGTH: 24
<212> TYPE: PRT
<213> ORGANISM: Artificial Sequence
<220> FEATURE:
<223> OTHER INFORMATION: 3Ab VH FW1

<400> SEQUENCE: 29

Gly Glu Leu Gln Glu Ser Gly Pro Gln Val Val Arg Pro Gly Thr Ser
1               5                   10                  15

Val Lys Ile Ser Cys Lys Ala Ser
            20

<210> SEQ ID NO 30
<211> LENGTH: 10
<212> TYPE: PRT
<213> ORGANISM: Artificial Sequence
<220> FEATURE:
<223> OTHER INFORMATION: 3Ab VH CDR1

<400> SEQUENCE: 30

Gly Tyr Ser Phe Ser Asn Tyr Trp Met His
1               5                   10

<210> SEQ ID NO 31
<211> LENGTH: 14
<212> TYPE: PRT
<213> ORGANISM: Artificial Sequence
<220> FEATURE:
<223> OTHER INFORMATION: 3Ab VH FW2

<400> SEQUENCE: 31

Trp Val Lys Gln Arg Pro Gly Gln Gly Leu Glu Trp Ile Gly
1               5                   10

<210> SEQ ID NO 32
<211> LENGTH: 17
<212> TYPE: PRT
<213> ORGANISM: Artificial Sequence
<220> FEATURE:
<223> OTHER INFORMATION: 3Ab VH CDR2

<400> SEQUENCE: 32

Val Ile Asp Pro Ser Asp Ser Glu Thr Arg Leu Asn Gln Lys Phe Lys
1               5                   10                  15

Asp

<210> SEQ ID NO 33
<211> LENGTH: 32
<212> TYPE: PRT
<213> ORGANISM: Artificial Sequence
<220> FEATURE:
<223> OTHER INFORMATION: 3Ab VH FW3

<400> SEQUENCE: 33

Lys Ala Thr Leu Thr Val Asp Lys Ser Ser Ser Thr Ala Tyr Met Gln
1               5                   10                  15

Leu Ser Ser Pro Thr Ser Glu Asp Ser Ala Ile Tyr Tyr Cys Ala Arg
                20                  25                  30

<210> SEQ ID NO 34
<211> LENGTH: 9
<212> TYPE: PRT
<213> ORGANISM: Artificial Sequence
<220> FEATURE:
<223> OTHER INFORMATION: 3Ab VH CDR3

<400> SEQUENCE: 34

Ser Gln Phe Gly Leu Arg Phe Ala Tyr
1               5

<210> SEQ ID NO 35
<211> LENGTH: 11
<212> TYPE: PRT
<213> ORGANISM: Artificial Sequence
<220> FEATURE:
<223> OTHER INFORMATION: 3Ab VH FW4

<400> SEQUENCE: 35

Trp Gly Gln Gly Thr Leu Val Thr Val Ser Ala
1               5                   10

<210> SEQ ID NO 36
<211> LENGTH: 23
<212> TYPE: PRT
<213> ORGANISM: Artificial Sequence
<220> FEATURE:
<223> OTHER INFORMATION: 3Ab VL FW1

<400> SEQUENCE: 36

Asp Ile Val Met Thr Gln Ser Pro Ser Ser Met Thr Val Thr Ala Gly
1               5                   10                  15

Glu Lys Val Thr Met Ser Cys
            20

<210> SEQ ID NO 37
<211> LENGTH: 17
<212> TYPE: PRT
<213> ORGANISM: Artificial Sequence
<220> FEATURE:
<223> OTHER INFORMATION: 3Ab VL CDR1

<400> SEQUENCE: 37

Gln Ser Ser Gln Ser Leu Phe Asn Ser Gly Thr Gln Lys Asn Tyr Leu
1               5                   10                  15

Thr

<210> SEQ ID NO 38
<211> LENGTH: 15
<212> TYPE: PRT
<213> ORGANISM: Artificial Sequence
<220> FEATURE:
<223> OTHER INFORMATION: 3Ab VL FW2

<400> SEQUENCE: 38

Trp Tyr Gln Gln Lys Pro Gly Gln Pro Pro Lys Leu Leu Ile Ser
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: 3Ab VL CDR2

<400> SEQUENCE: 39

Trp Ala Ser Thr Arg Asp Ser
1               5

<210> SEQ ID NO 40
<211> LENGTH: 32

```
<212> TYPE: PRT
<213> ORGANISM: Artificial Sequence
<220> FEATURE:
<223> OTHER INFORMATION: 3Ab VL FW3

<400> SEQUENCE: 40

Gly Val Pro Asp Arg Phe Thr Gly Ser Gly Ser Gly Thr Asp Phe Thr
1               5                   10                  15

Leu Thr Ile Asn Gly Val Gln Ala Glu Asp Leu Ala Val Tyr Phe Cys
            20                  25                  30

<210> SEQ ID NO 41
<211> LENGTH: 9
<212> TYPE: PRT
<213> ORGANISM: Artificial Sequence
<220> FEATURE:
<223> OTHER INFORMATION: 3Ab VL CDR3

<400> SEQUENCE: 41

Gln Asn Asp Tyr Asp Ser Pro Tyr Thr
1               5

<210> SEQ ID NO 42
<211> LENGTH: 11
<212> TYPE: PRT
<213> ORGANISM: Artificial Sequence
<220> FEATURE:
<223> OTHER INFORMATION: 3Ab VL FW4

<400> SEQUENCE: 42

Phe Gly Gly Gly Thr Lys Leu Glu Ile Lys Arg
1               5                   10

<210> SEQ ID NO 43
<211> LENGTH: 25
<212> TYPE: PRT
<213> ORGANISM: Artificial Sequence
<220> FEATURE:
<223> OTHER INFORMATION: 4Ab VH FW1

<400> SEQUENCE: 43

Glu Val Gln Leu Gln Gln Ser Gly Pro Glu Leu Val Lys Pro Gly Ala
1               5                   10                  15

Ser Val Lys Ile Ser Cys Lys Ala Ser
            20                  25

<210> SEQ ID NO 44
<211> LENGTH: 10
<212> TYPE: PRT
<213> ORGANISM: Artificial Sequence
<220> FEATURE:
<223> OTHER INFORMATION: 4Ab VH CDR1

<400> SEQUENCE: 44

Gly Tyr Thr Phe Thr Asp Tyr Asn Ile His
1               5                   10

<210> SEQ ID NO 45
<211> LENGTH: 14
<212> TYPE: PRT
<213> ORGANISM: Artificial Sequence
<220> FEATURE:
<223> OTHER INFORMATION: 4Ab VH FW2

<400> SEQUENCE: 45

Trp Val Lys Gln Ser Pro Gly Lys Ser Leu Glu Trp Ile Gly
```

<210> SEQ ID NO 46
<211> LENGTH: 17
<212> TYPE: PRT
<213> ORGANISM: Artificial Sequence
<220> FEATURE:
<223> OTHER INFORMATION: 4Ab VH CDR2

<400> SEQUENCE: 46

```
Tyr Ile Tyr Pro Asp Asn Gly Asp Thr Gly Tyr Asn Gln Ile Phe Lys
1               5                   10                  15
Asn
```

<210> SEQ ID NO 47
<211> LENGTH: 32
<212> TYPE: PRT
<213> ORGANISM: Artificial Sequence
<220> FEATURE:
<223> OTHER INFORMATION: 4Ab VH FW3

<400> SEQUENCE: 47

```
Lys Ala Thr Leu Thr Val Asp Thr Ser Ser Ser Ala Ala Tyr Met Glu
1               5                   10                  15
Leu Arg Ser Leu Thr Ser Glu Asp Ser Ala Val Tyr Tyr Cys Val Arg
                20                  25                  30
```

<210> SEQ ID NO 48
<211> LENGTH: 6
<212> TYPE: PRT
<213> ORGANISM: Artificial Sequence
<220> FEATURE:
<223> OTHER INFORMATION: 4Ab VH CDR3

<400> SEQUENCE: 48

```
Arg Val Leu Leu Asp Ser
1               5
```

<210> SEQ ID NO 49
<211> LENGTH: 11
<212> TYPE: PRT
<213> ORGANISM: Artificial Sequence
<220> FEATURE:
<223> OTHER INFORMATION: 4Ab VH FW4

<400> SEQUENCE: 49

```
Trp Gly Gln Gly Thr Ser Val Thr Val Ser Ser
1               5                   10
```

<210> SEQ ID NO 50
<211> LENGTH: 23
<212> TYPE: PRT
<213> ORGANISM: Artificial Sequence
<220> FEATURE:
<223> OTHER INFORMATION: 4Ab VL FW1

<400> SEQUENCE: 50

```
Asp Ile Gln Met Thr Gln Thr Thr Ser Ser Leu Ser Ala Ser Leu Gly
1               5                   10                  15
Asp Arg Val Thr Ile Ser Cys
                20
```

<210> SEQ ID NO 51
<211> LENGTH: 11
<212> TYPE: PRT

<213> ORGANISM: Artificial Sequence
<220> FEATURE:
<223> OTHER INFORMATION: 4Ab VL CDR1

<400> SEQUENCE: 51

Ser Ala Ser Gln Asp Ile Asn Asn Phe Leu Asn
1               5                   10

<210> SEQ ID NO 52
<211> LENGTH: 15
<212> TYPE: PRT
<213> ORGANISM: Artificial Sequence
<220> FEATURE:
<223> OTHER INFORMATION: 4Ab VL FW2

<400> SEQUENCE: 52

Trp Tyr Gln Gln Lys Pro Asp Gly Thr Ile Lys Leu Leu Ile Tyr
1               5                   10                  15

<210> SEQ ID NO 53
<211> LENGTH: 7
<212> TYPE: PRT
<213> ORGANISM: Artificial Sequence
<220> FEATURE:
<223> OTHER INFORMATION: 4Ab VL CDR2

<400> SEQUENCE: 53

Tyr Thr Ser Ser Leu Gln Ser
1               5

<210> SEQ ID NO 54
<211> LENGTH: 32
<212> TYPE: PRT
<213> ORGANISM: Artificial Sequence
<220> FEATURE:
<223> OTHER INFORMATION: 4Ab VL FW3

<400> SEQUENCE: 54

Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Thr Tyr Tyr Cys
                20                  25                  30

<210> SEQ ID NO 55
<211> LENGTH: 9
<212> TYPE: PRT
<213> ORGANISM: Artificial Sequence
<220> FEATURE:
<223> OTHER INFORMATION: 4Ab VL CDR3

<400> SEQUENCE: 55

Gln Gln Tyr Ser Lys Leu Pro Arg Thr
1               5

<210> SEQ ID NO 56
<211> LENGTH: 11
<212> TYPE: PRT
<213> ORGANISM: Artificial Sequence
<220> FEATURE:
<223> OTHER INFORMATION: 4Ab VL FW4

<400> SEQUENCE: 56

Phe Gly Gly Gly Thr Lys Leu Glu Ile Lys Arg
1               5                   10

<210> SEQ ID NO 57

```
<211> LENGTH: 25
<212> TYPE: PRT
<213> ORGANISM: Artificial Sequence
<220> FEATURE:
<223> OTHER INFORMATION: 5Ab VH FW1

<400> SEQUENCE: 57

Glu Val Gln Leu Gln Gln Ser Gly Gly Gly Leu Val Gln Pro Gly Gly
1               5                   10                  15
Ser Leu Lys Leu Ser Cys Ala Ala Ser
            20                  25

<210> SEQ ID NO 58
<211> LENGTH: 10
<212> TYPE: PRT
<213> ORGANISM: Artificial Sequence
<220> FEATURE:
<223> OTHER INFORMATION: 5Ab VH CDR1

<400> SEQUENCE: 58

Gly Phe Thr Phe Ser Asn Tyr Asp Met Ser
1               5                   10

<210> SEQ ID NO 59
<211> LENGTH: 14
<212> TYPE: PRT
<213> ORGANISM: Artificial Sequence
<220> FEATURE:
<223> OTHER INFORMATION: 5Ab VH FW2

<400> SEQUENCE: 59

Trp Ile Arg Gln Thr Pro Asp Lys Arg Leu Glu Met Val Ala
1               5                   10

<210> SEQ ID NO 60
<211> LENGTH: 17
<212> TYPE: PRT
<213> ORGANISM: Artificial Sequence
<220> FEATURE:
<223> OTHER INFORMATION: 5Ab VH CDR2

<400> SEQUENCE: 60

Ala Ile Asn Ser Asn Gly Gly Ser Thr Tyr Tyr Pro Asp Ser Val Lys
1               5                   10                  15
Gly

<210> SEQ ID NO 61
<211> LENGTH: 32
<212> TYPE: PRT
<213> ORGANISM: Artificial Sequence
<220> FEATURE:
<223> OTHER INFORMATION: 5Ab VH FW3

<400> SEQUENCE: 61

Arg Phe Thr Ile Ser Arg Asp Lys Ala Lys Asn Thr Leu Tyr Leu Gln
1               5                   10                  15
Met Ser Ser Leu Lys Ser Glu Asp Thr Ala Met Tyr Tyr Cys Ala Ser
            20                  25                  30

<210> SEQ ID NO 62
<211> LENGTH: 9
<212> TYPE: PRT
<213> ORGANISM: Artificial Sequence
<220> FEATURE:
<223> OTHER INFORMATION: 5Ab VH CDR3
```

<400> SEQUENCE: 62

Pro Asn Gly Tyr Gly Ala Met Asp Tyr
1               5

<210> SEQ ID NO 63
<211> LENGTH: 11
<212> TYPE: PRT
<213> ORGANISM: Artificial Sequence
<220> FEATURE:
<223> OTHER INFORMATION: 5Ab VH FW4

<400> SEQUENCE: 63

Trp Gly Gln Gly Thr Ser Val Thr Val Ser Ser
1               5                   10

<210> SEQ ID NO 64
<211> LENGTH: 23
<212> TYPE: PRT
<213> ORGANISM: Artificial Sequence
<220> FEATURE:
<223> OTHER INFORMATION: 5Ab VL FW1

<400> SEQUENCE: 64

Asp Ile Val Ile Thr Gln Thr Pro Leu Thr Leu Ser Val Thr Ile Gly
1               5                   10                  15

Gln Pro Ala Ser Ile Ser Cys
            20

<210> SEQ ID NO 65
<211> LENGTH: 16
<212> TYPE: PRT
<213> ORGANISM: Artificial Sequence
<220> FEATURE:
<223> OTHER INFORMATION: 5Ab VL CDR1

<400> SEQUENCE: 65

Lys Ser Arg Gln Ser Leu Leu Asp Ser Asp Gly Lys Thr Tyr Leu Asn
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: 5Ab VL FW2

<400> SEQUENCE: 66

Trp Leu Leu Gln Arg Pro Gly Glu Ser Pro Lys Leu Leu Ile Tyr
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: 5Ab VL CDR2

<400> SEQUENCE: 67

Leu Val Ser Lys Leu Asp Ser
1               5

<210> SEQ ID NO 68
<211> LENGTH: 32
<212> TYPE: PRT
<213> ORGANISM: Artificial Sequence
<220> FEATURE:

<223> OTHER INFORMATION: 5Ab VL FW3

<400> SEQUENCE: 68

Gly Val Pro Asp Arg Phe Thr Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 69
<211> LENGTH: 9
<212> TYPE: PRT
<213> ORGANISM: Artificial Sequence
<220> FEATURE:
<223> OTHER INFORMATION: 5Ab VL CDR3

<400> SEQUENCE: 69

Leu Gln Ala Thr His Phe Pro Trp Thr
1               5

<210> SEQ ID NO 70
<211> LENGTH: 12
<212> TYPE: PRT
<213> ORGANISM: Artificial Sequence
<220> FEATURE:
<223> OTHER INFORMATION: 5Ab VL FW4

<400> SEQUENCE: 70

Phe Gly Gly Gly Thr Lys Leu Glu Ile Lys Arg Ala
1               5                   10

<210> SEQ ID NO 71
<211> LENGTH: 118
<212> TYPE: PRT
<213> ORGANISM: Artificial Sequence
<220> FEATURE:
<223> OTHER INFORMATION: 1Ab VH

<400> SEQUENCE: 71

Glu Val Lys Leu Gln Glu Ser Gly Ala Glu Leu Ala Lys Pro Gly Ala
1               5                   10                  15

Ser Val Lys Met Ser Cys Arg Ala Ser Gly Tyr Thr Phe Thr Ser Tyr
            20                  25                  30

Trp Ile His Trp Val Lys Glu Arg Pro Gly Gln Gly Leu Glu Trp Ile
        35                  40                  45

Gly Tyr Ile Thr Pro Asn Thr Gly Tyr Asn Glu Asn Ser Gln Lys Phe
    50                  55                  60

Arg Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Val Arg Arg Thr Tyr Glu Gly Tyr Leu Asp Val Trp Gly Ala Gly Thr
            100                 105                 110

Thr Val Thr Val Ser Ser
        115

<210> SEQ ID NO 72
<211> LENGTH: 113
<212> TYPE: PRT
<213> ORGANISM: Artificial Sequence
<220> FEATURE:
<223> OTHER INFORMATION: 1Ab VL

<400> SEQUENCE: 72

```
Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Asn Leu Val His Asn
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Asn Ile
65              70                  75                  80

Ser Arg Val Glu Ala Glu Asp Leu Gly Ile Tyr Tyr Cys Phe Gln Ala
                85                  90                  95

Ser His Val Pro Arg Thr Phe Gly Gly Gly Thr Lys Leu Glu Ile Lys
            100                 105                 110

Arg
```

```
<210> SEQ ID NO 73
<211> LENGTH: 120
<212> TYPE: PRT
<213> ORGANISM: Artificial Sequence
<220> FEATURE:
<223> OTHER INFORMATION: 2Ab VH

<400> SEQUENCE: 73

Glu Val Gln Leu Gln Glu Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Val Leu Glu Trp Ile
        35                  40                  45

Gly Tyr Ile Asn Pro Asn Thr Gly Phe Thr Glu Tyr Ser Gln Lys Phe
    50                  55                  60

Lys Asp Lys Ala Thr Leu Thr Ala Val Lys Ser Ser Ser Thr Ala Tyr
65              70                  75                  80

Ile Gln Leu Thr Ser Leu Thr Ser Asp Asp Ser Ala Val Tyr Tyr Cys
                85                  90                  95

Ala Arg Glu Asn Tyr Arg Tyr Asp Gly Ala Met Asp Tyr Trp Gly Gln
            100                 105                 110

Gly Thr Ser Val Thr Val Ser Ser
        115                 120
```

```
<210> SEQ ID NO 74
<211> LENGTH: 109
<212> TYPE: PRT
<213> ORGANISM: Artificial Sequence
<220> FEATURE:
<223> OTHER INFORMATION: 2Ab VL

<400> SEQUENCE: 74

Asp Ile Val Leu Thr Gln Ser Pro Ala Leu Met Ala Ala Phe Pro Gly
1               5                   10                  15

Asp Arg Val Thr Ile Thr Cys Ser Val Ser Ser Ser Val Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Thr Leu Ala Ser Gly Val Pro Val Arg Phe Ser
    50                  55                  60
```

```
Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Ser Tyr Pro
                 85                  90                  95

Leu Thr Phe Gly Ala Gly Thr Lys Leu Glu Leu Lys Arg
            100                 105
```

<210> SEQ ID NO 75
<211> LENGTH: 117
<212> TYPE: PRT
<213> ORGANISM: Artificial Sequence
<220> FEATURE:
<223> OTHER INFORMATION: 3Ab VH

<400> SEQUENCE: 75

```
Gly Glu Leu Gln Glu Ser Gly Pro Gln Val Val Arg Pro Gly Thr Ser
 1               5                  10                  15

Val Lys Ile Ser Cys Lys Ala Ser Gly Tyr Ser Phe Ser Asn Tyr Trp
             20                  25                  30

Met His Trp Val Lys Gln Arg Pro Gly Gln Gly Leu Glu Trp Ile Gly
         35                  40                  45

Val Ile Asp Pro Ser Asp Ser Glu Thr Arg Leu Asn Gln Lys Phe Lys
 50                  55                  60

Asp Lys Ala Thr Leu Thr Val Asp Lys Ser Ser Thr Ala Tyr Met
 65                  70                  75                  80

Gln Leu Ser Ser Pro Thr Ser Glu Asp Ser Ala Ile Tyr Tyr Cys Ala
                 85                  90                  95

Arg Ser Gln Phe Gly Leu Arg Phe Ala Tyr Trp Gly Gln Gly Thr Leu
            100                 105                 110

Val Thr Val Ser Ala
            115
```

<210> SEQ ID NO 76
<211> LENGTH: 114
<212> TYPE: PRT
<213> ORGANISM: Artificial Sequence
<220> FEATURE:
<223> OTHER INFORMATION: 3Ab VL

<400> SEQUENCE: 76

```
Asp Ile Val Met Thr Gln Ser Pro Ser Ser Met Thr Val Thr Ala Gly
 1               5                  10                  15

Glu Lys Val Thr Met Ser Cys Gln Ser Ser Gln Ser Leu Phe Asn Ser
             20                  25                  30

Gly Thr Gln Lys Asn Tyr Leu Thr Trp Tyr Gln Gln Lys Pro Gly Gln
         35                  40                  45

Pro Pro Lys Leu Leu Ile Ser Trp Ala Ser Thr Arg Asp Ser Gly Val
 50                  55                  60

Pro Asp Arg Phe Thr Gly Ser Gly Ser Gly Thr Asp Phe Thr Leu Thr
 65                  70                  75                  80

Ile Asn Gly Val Gln Ala Glu Asp Leu Ala Val Tyr Phe Cys Gln Asn
                 85                  90                  95

Asp Tyr Asp Ser Pro Tyr Thr Phe Gly Gly Gly Thr Lys Leu Glu Ile
            100                 105                 110

Lys Arg
```

<210> SEQ ID NO 77

```
<211> LENGTH: 115
<212> TYPE: PRT
<213> ORGANISM: Artificial Sequence
<220> FEATURE:
<223> OTHER INFORMATION: 4Ab VH

<400> SEQUENCE: 77

Glu Val Gln Leu Gln Gln Ser Gly Pro Glu Leu Val Lys Pro Gly Ala
1               5                  10                  15

Ser Val Lys Ile Ser Cys Lys Ala Ser Gly Tyr Thr Phe Thr Asp Tyr
            20                  25                  30

Asn Ile His Trp Val Lys Gln Ser Pro Gly Lys Ser Leu Glu Trp Ile
        35                  40                  45

Gly Tyr Ile Tyr Pro Asp Asn Gly Asp Thr Gly Tyr Asn Gln Ile Phe
    50                  55                  60

Lys Asn Lys Ala Thr Leu Thr Val Asp Thr Ser Ser Ala Ala Tyr
65                  70                  75                  80

Met Glu Leu Arg Ser Leu Thr Ser Glu Asp Ser Ala Val Tyr Tyr Cys
                85                  90                  95

Val Arg Arg Val Leu Leu Asp Ser Trp Gly Gln Gly Thr Ser Val Thr
            100                 105                 110

Val Ser Ser
        115

<210> SEQ ID NO 78
<211> LENGTH: 108
<212> TYPE: PRT
<213> ORGANISM: Artificial Sequence
<220> FEATURE:
<223> OTHER INFORMATION: 4Ab VL

<400> SEQUENCE: 78

Asp Ile Gln Met Thr Gln Thr Thr Ser Ser Leu Ser Ala Ser Leu Gly
1               5                  10                  15

Asp Arg Val Thr Ile Ser Cys Ser Ala Ser Gln Asp Ile Asn Asn Phe
            20                  25                  30

Leu Asn Trp Tyr Gln Gln Lys Pro Asp Gly Thr Ile Lys Leu Leu Ile
        35                  40                  45

Tyr Tyr Thr Ser Ser Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Arg
                85                  90                  95

Thr Phe Gly Gly Gly Thr Lys Leu Glu Ile Lys Arg
            100                 105

<210> SEQ ID NO 79
<211> LENGTH: 118
<212> TYPE: PRT
<213> ORGANISM: Artificial Sequence
<220> FEATURE:
<223> OTHER INFORMATION: 5Ab VH

<400> SEQUENCE: 79

Glu Val Gln Leu Gln Gln Ser Gly Gly Gly Leu Val Gln Pro Gly Gly
1               5                  10                  15

Ser Leu Lys Leu Ser Cys Ala Ser Gly Phe Thr Phe Ser Asn Tyr
            20                  25                  30
```

Asp Met Ser Trp Ile Arg Gln Thr Pro Asp Lys Arg Leu Glu Met Val
                35                  40                  45

Ala Ala Ile Asn Ser Asn Gly Gly Ser Thr Tyr Tyr Pro Asp Ser Val
 50                  55                  60

Lys Gly Arg Phe Thr Ile Ser Arg Asp Lys Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Ala Ser Pro Asn Gly Tyr Gly Ala Met Asp Tyr Trp Gly Gln Gly Thr
            100                 105                 110

Ser Val Thr Val Ser Ser
            115

<210> SEQ ID NO 80
<211> LENGTH: 114
<212> TYPE: PRT
<213> ORGANISM: Artificial Sequence
<220> FEATURE:
<223> OTHER INFORMATION: 5Ab VL

<400> SEQUENCE: 80

Asp Ile Val Ile Thr Gln Thr Pro Leu Thr Leu Ser Val Thr Ile Gly
 1               5                  10                  15

Gln Pro Ala Ser Ile Ser Cys Lys Ser Arg Gln Ser Leu Leu Asp Ser
                20                  25                  30

Asp Gly Lys Thr Tyr Leu Asn Trp Leu Leu Gln Arg Pro Gly Glu Ser
                35                  40                  45

Pro Lys Leu Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Leu Gln Ala
                85                  90                  95

Thr His Phe Pro Trp Thr Phe Gly Gly Gly Thr Lys Leu Glu Ile Lys
            100                 105                 110

Arg Ala

<210> SEQ ID NO 81
<211> LENGTH: 354
<212> TYPE: DNA
<213> ORGANISM: Artificial Sequence
<220> FEATURE:
<223> OTHER INFORMATION: 1Ab VH DNA

<400> SEQUENCE: 81
gaggtcaaac tgcaggagtc tggggctgaa ctggcaaaac ctggggcctc agtgaagatg        60
tcctgcaggg cttctggcta cacctttacc agctattgga tacactgggt gaagagagg       120 cctggacagg gtctggaatg gattggatac attactccta atacaggtta taatgagaac       180
agtcagaagt tcaggggcaa ggccacattg actgcagaca atcctccaa cacagcttat       240 atgcaactaa gcagcctgac atctgaggac tctgcagtct atttctgtgt aagaaggacg       300 tatgagggt acctcgatgt ctgggcgca gggaccacgg tcaccgtctc ctca              354

<210> SEQ ID NO 82
<211> LENGTH: 339
<212> TYPE: DNA
<213> ORGANISM: Artificial Sequence
<220> FEATURE:

<223> OTHER INFORMATION: 1Ab VL DNA

<400> SEQUENCE: 82

| gacattgtga tgacccaaac tccactctcc ctgcctgtca gtcttggaga tcaagcctcc | 60 |
| atctcttgca gatctagtca gaaccttgta cataataatg aaacacccta tttagagtgg | 120 |
| tacctgcaga accaggccag gtctccaaag ctcctgatct acaaagtttc caaccgattg | 180 |
| tctggggtcc cagacaggtt cagtggcagt ggatccggga cagacttcac actcaatatc | 240 |
| agcagagtgg aggctgagga tctgggaatt tattactgct ttcaggcttc acatgttcct | 300 |
| cggacgttcg gtggaggcac caagctggaa atcaaacgg | 339 |

<210> SEQ ID NO 83
<211> LENGTH: 360
<212> TYPE: DNA
<213> ORGANISM: Artificial Sequence
<220> FEATURE:
<223> OTHER INFORMATION: 2Ab VH DNA

<400> SEQUENCE: 83

| gaggtgcagc tgcaggagtc aggggctgaa ctggcaaaac ctggggcctc agtgaagatg | 60 |
| tcctgcaagg cttctggcta cacctttact agctactgga tgcactgggt aaaacagagg | 120 |
| cctggacagg ttctggaatg gattggatac attaatccta atactggttt tactgaatat | 180 |
| agtcagaaat tcaaggacaa ggccacattg actgcagtca gtcctccag cacagcctat | 240 |
| atacaactga ccagcctgac atctgatgac tctgcagtct attactgtgc aagagagaac | 300 |
| tataggtacg acggggctat ggactactgg ggtcaaggaa cctcagtcac cgtctcctca | 360 |

<210> SEQ ID NO 84
<211> LENGTH: 327
<212> TYPE: DNA
<213> ORGANISM: Artificial Sequence
<220> FEATURE:
<223> OTHER INFORMATION: 2Ab VL DNA

<400> SEQUENCE: 84

| gatattgtgc taactcagtc tccagcactc atggctgcat ttccagggga cagggtcacc | 60 |
| atcacctgca gtgtcagctc aagtgtaagt tccagcaact gcactggta ccaacagaag | 120 |
| tcagaaaccct cccccaaaac ctggatttat ggcacatcca ccctggcttc tggagtccct | 180 |
| gttcgcttca gtggcagtgg atctgggacc tcttattctc tcacaatcag cagcatggag | 240 |
| gctgaagatg ctgccactta ttactgtcaa cagtggagta gttacccact cacgttcggt | 300 |
| gctgggacca agctggagct gaaacgg | 327 |

<210> SEQ ID NO 85
<211> LENGTH: 351
<212> TYPE: DNA
<213> ORGANISM: Artificial Sequence
<220> FEATURE:
<223> OTHER INFORMATION: 3Ab VH DNA

<400> SEQUENCE: 85

| ggtgaactgc aggagtcagg gcctcaggtg gttaggcctg ggacttcagt gaagatatcc | 60 |
| tgcaaggctt ctggttattc attttccaac tactggatgc actgggtgaa gcagaggcct | 120 |
| ggacaaggtc ttgagtggat tggcgtgatt gatccttccg atagtgaaac tagattaaat | 180 |
| cagaagttca aggacaaggc cacattgact gtagacaaat cctccagtac agcctacatg | 240 |
| caactcagca gcccgacatc tgaggactct gcgatctatt attgtgcaag atcacagttc | 300 |

```
gggctacgtt tgcttactg gggccaaggg actctggtca ctgtctctgc a            351
```

<210> SEQ ID NO 86
<211> LENGTH: 342
<212> TYPE: DNA
<213> ORGANISM: Artificial Sequence
<220> FEATURE:
<223> OTHER INFORMATION: 3Ab VL DNA

<400> SEQUENCE: 86

```
gacattgtga tgacccagtc tccatcctcc atgactgtga cagcaggaga gaaggtcact   60
atgagctgcc agtccagtca gagtctattc aacagtggaa ctcaaaagaa ctacttgacc  120
tggtaccagc agaaaccagg acagcctcct aaactgttga tctcctgggc atccactagg  180
gattctgggg tccctgatcg cttcacaggc agtggatctg gaacagattt cactctcacc  240
attaacggtg tgcaggctga agacctggca gtttatttct gtcagaatga ttatgattct  300
ccgtacacgt tcggagggggg acgaagctgg aaataaaac gg                     342
```

<210> SEQ ID NO 87
<211> LENGTH: 345
<212> TYPE: DNA
<213> ORGANISM: Artificial Sequence
<220> FEATURE:
<223> OTHER INFORMATION: 4Ab VH DNA

<400> SEQUENCE: 87

```
gaggtgcaac tgcagcagtc aggacctgag ctggtgaaac ctggggcctc agtgaagata   60
tcctgcaagg cttctggata cacattcact gactacaaca tacactgggt gaaacagagc  120
cctggaaaga gccttgagtg gattggatat atttatcctg acaatggtga atactggctac 180
aaccagattt tcaagaacaa ggccacattg actgtagaca cttcgtccag cgcagcctac  240
atggaactcc gcagcctgac atctgaggac tctgcagtct attactgtgt aagacgggtc  300
cttttggact cctggggtca aggaacctca gtcaccgtct cctca                  345
```

<210> SEQ ID NO 88
<211> LENGTH: 324
<212> TYPE: DNA
<213> ORGANISM: Artificial Sequence
<220> FEATURE:
<223> OTHER INFORMATION: 4Ab VL DNA

<400> SEQUENCE: 88

```
gatatccaga tgacacagac tacatcttcc ctgtctgcct ctctgggaga cagagtcacc   60
atcagttgca gtgcaagtca ggacattaac aattttttaa actggtatca gcagaaacca  120
gatggaacta ttaaactcct gatctattac acatcaagtt tacagtcagg agtcccgtca  180
aggttcagtg gcagtgggtc tgggacagat tattctctca ccatcagcaa cctggaacct  240
gaagatattg ccacttacta ttgtcaacaa tatagtaaac ttcctcggac gttcggtgga  300
ggcaccaagc tggaaatcaa acgg                                         324
```

<210> SEQ ID NO 89
<211> LENGTH: 354
<212> TYPE: DNA
<213> ORGANISM: Artificial Sequence
<220> FEATURE:
<223> OTHER INFORMATION: 5Ab VH DNA

<400> SEQUENCE: 89

```
gaggtgcagc tgcagcagtc aggggggaggc ttagtgcagc ctggagggtc cctgaaactc        60
tcctgtgcag cctctggatt cactttcagt aactatgaca tgtcttggat tcgccagact       120
ccagacaaga ggctggagat ggtcgcagcc attaatagta atggtggtag cacctattat       180
ccagacagtg tgaagggccg attcaccatc tccagagaca aagccaagaa cacccctatac      240 ctgcaaatga gcagtctgaa gtctgaggac acagccatgt attactgtgc gagccctaat       300
ggttacggag ctatggacta ctggggtcaa ggaacctcag tcaccgtctc ctca             354

<210> SEQ ID NO 90
<211> LENGTH: 339
<212> TYPE: DNA
<213> ORGANISM: Artificial Sequence
<220> FEATURE:
<223> OTHER INFORMATION: 5Ab VL DNA

<400> SEQUENCE: 90
gatattgtga taacccagac tccactcact ttgtcggtta ccattggaca accagcttcc        60
atctcttgca agtcacgtca gagcctctta gatagtgatg gaaaaaccta tttaaattgg       120
ttattacaga ggccaggcga gtctccaaag ctcctaatct atctggtgtc taaactggac       180
tctggagtcc ctgacaggtt cactggcagt ggatcaggga cagatttcac actgaaaatc       240
agcagagtgg aggctgagga tttgggagtt tattactgct tgcaagctac acattttccg       300
tggacgttcg gtggaggcac caagctggaa atcaaacgg                             339
```